United States Patent [19]

Prosl et al.

[11] Patent Number: 5,989,206
[45] Date of Patent: Nov. 23, 1999

[54] APPARATUS AND METHOD FOR THE DIALYSIS OF BLOOD

[75] Inventors: Frank R. Prosl, Duxbury; Brian K. Estabrook, Foxboro, both of Mass.

[73] Assignee: Biolink Corporation, Middleboro, Mass.

[21] Appl. No.: 08/962,164

[22] Filed: Oct. 31, 1997

[51] Int. Cl.[6] .......................... A61M 37/00; A61M 11/00; A61M 5/00; A61M 25/00
[52] U.S. Cl. ..................................... 604/5; 604/4; 604/93; 604/523; 604/264
[58] Field of Search ............................. 604/4, 5, 93, 523, 604/264

[56]     References Cited

U.S. PATENT DOCUMENTS

| B2 Re. 31,873 | 9/1989 | Howes ..................................... 128/674 |
| 274,447 | 3/1883 | Kennish . |
| 3,331,371 | 7/1967 | Rocchi et al. .......................... 128/349 |
| 3,888,249 | 6/1975 | Spencer .................................. 128/214 |
| 3,952,747 | 4/1976 | Kimmell, Jr. ........................... 128/303 |
| 4,108,173 | 8/1978 | Slivenko et al. ....................... 128/214 |
| 4,243,034 | 1/1981 | Brandt ................................. 128/214.4 |
| 4,403,983 | 9/1983 | Edelman et al. .......................... 604/43 |
| 4,417,888 | 11/1983 | Cosentino et al. ...................... 604/175 |
| 4,484,912 | 11/1984 | Raible .................................... 604/175 |
| 4,493,696 | 1/1985 | Uldall ...................................... 604/43 |
| 4,496,350 | 1/1985 | Cosentino ............................... 604/175 |
| 4,543,088 | 9/1985 | Bootman et al. ......................... 604/93 |
| 4,548,597 | 10/1985 | Nelson ..................................... 604/43 |
| 4,549,879 | 10/1985 | Groshong et al. ...................... 604/247 |
| 4,568,329 | 2/1986 | Mahurkar ................................. 604/43 |
| 4,657,536 | 4/1987 | Dorman ................................. 604/247 |
| 4,671,796 | 6/1987 | Groshong et al. ...................... 604/247 |
| 4,673,394 | 6/1987 | Fenton, Jr. et al. ..................... 604/175 |
| 4,685,905 | 8/1987 | Jeanneret nee Aab ................. 604/247 |
| 4,692,146 | 9/1987 | Hilger ...................................... 604/93 |
| 4,701,166 | 10/1987 | Groshong et al. ...................... 604/247 |
| 4,704,103 | 11/1987 | Stober et al. ............................ 604/175 |
| 4,705,501 | 11/1987 | Wigness et al. .......................... 604/43 |
| 4,759,752 | 7/1988 | Stober .................................... 604/247 |
| 4,772,270 | 9/1988 | Wiita et al. ............................. 604/175 |
| 4,802,885 | 2/1989 | Weeks et al. .............................. 694/93 |
| 4,808,155 | 2/1989 | Mahurkar ................................. 604/43 |
| 4,846,791 | 7/1989 | Hattler et al. ............................. 604/43 |
| 4,846,806 | 7/1989 | Wigness et al. ........................ 604/175 |
| 4,892,518 | 1/1990 | Cupp et al. ............................... 604/93 |
| 4,898,669 | 2/1990 | Tesio ....................................... 210/232 |
| 4,973,319 | 11/1990 | Melsky ................................... 604/247 |
| 4,994,042 | 2/1991 | Vadher ................................... 605/165 |

(List continued on next page.)

FOREIGN PATENT DOCUMENTS 9625196  8/1996  WIPO .

OTHER PUBLICATIONS

"lettres", La Presse Medicale, 4 avril 1992, 2 pages, including translation.
"A New Vascular Access Catheter for Hedmodialysis", American Journal of Kidney Diseases, vol. 21, No. 3, (Mar.), 8 pages 1993.
"Central venous catheters for haemodialysis: looking for optimal blood flow", European Renal Association—European Dialysis and Transplant Association, 1997, 3 pages.
"Fibrin Sheet Covering Subclavian or Femoral Dialysis Catheters", Artificial Organs, vol. 18, No. 4, 1994, 2 pages.
"Utilisation en hemodialyse chronique de la technique du site implantable", Nephrologie, vol. 15, No. 2, 1994, 4 pages, including translation.

Primary Examiner—Corrine McDermott
Assistant Examiner—Cheryl L. Huseman
Attorney, Agent, or Firm—Pandiscio & Pandiscio

[57]     ABSTRACT

Improved apparatus and method for the dialysis of blood. The improved apparatus comprises a subcutaneous port and catheter assembly comprising a connector portion comprising a subcutaneous port element, and a catheter portion comprising a catheter element. The improved apparatus also comprises a novel percutaneous catheter assembly comprising a catheter portion comprising a catheter element, and a connector portion comprising an extracorporeal connector element.

66 Claims, 23 Drawing Sheets

U.S. PATENT DOCUMENTS

| | | | |
|---|---|---|---|
| 5,030,210 | 7/1991 | Alchas | 604/247 |
| 5,041,098 | 8/1991 | Loiterman et al. | 604/175 |
| 5,053,004 | 10/1991 | Markel et al. | 604/43 |
| 5,057,084 | 10/1991 | Ensminger et al. | 604/167 |
| 5,106,368 | 4/1992 | Uldall et al. | 604/43 |
| 5,112,301 | 5/1992 | Fenton, Jr. et al. | 604/30 |
| 5,152,777 | 10/1992 | Goldberg et al. | 606/200 |
| 5,156,600 | 10/1992 | Young | 604/247 |
| 5,167,623 | 12/1992 | Cianci et al. | 604/43 |
| 5,167,638 | 12/1992 | Felix et al. | 604/175 |
| 5,171,216 | 12/1992 | Dasse et al. | 604/43 |
| 5,176,627 | 1/1993 | Watson | 604/8 |
| 5,176,653 | 1/1993 | Metais | 604/167 |
| 5,180,365 | 1/1993 | Ensminger et al. | 604/93 |
| 5,188,593 | 2/1993 | Martin | 604/43 |
| 5,197,951 | 3/1993 | Mahurkar | 604/93 |
| 5,197,976 | 3/1993 | Herweck et al. | 623/1 |
| 5,203,771 | 4/1993 | Melker et al. | 604/53 |
| 5,209,723 | 5/1993 | Twardowski et al. | 604/43 |
| 5,221,255 | 6/1993 | Mahurkar et al. | 604/43 |
| 5,224,938 | 7/1993 | Fenton, Jr. | 604/247 |
| 5,256,146 | 10/1993 | Ensminger et al. | 604/104 |
| 5,263,930 | 11/1993 | Ensminger | 604/93 |
| 5,290,263 | 3/1994 | Wigness et al. | 604/247 |
| 5,306,255 | 4/1994 | Haindl | 604/175 |
| 5,318,545 | 6/1994 | Tucker | 604/244 |
| 5,336,194 | 8/1994 | Polaschegg et al. | 604/175 |
| 5,346,471 | 9/1994 | Raulerson | 604/43 |
| 5,350,360 | 9/1994 | Ensminger et al. | 604/93 |
| 5,360,407 | 11/1994 | Leonard | 604/175 |
| 5,380,276 | 1/1995 | Miller et al. | 604/28 |
| 5,399,168 | 3/1995 | Wadsworth, Jr. et al. | 604/175 |
| 5,451,206 | 9/1995 | Young | 604/43 |
| 5,472,418 | 12/1995 | Palestrant | 604/43 |
| 5,486,159 | 1/1996 | Mahurakar | 604/4 |
| 5,509,900 | 4/1996 | Kirkman | 604/104 |
| 5,520,664 | 5/1996 | Bricault, Jr. et al. | 604/265 |
| 5,556,381 | 9/1996 | Ensminger | 604/93 |
| 5,562,617 | 10/1996 | Finch, Jr. et al. | 604/93 |
| 5,571,093 | 11/1996 | Cruz et al. | 604/270 |
| 5,624,413 | 4/1997 | Markel et al. | 604/280 |
| 5,685,867 | 11/1997 | Twardowski et al. | 604/280 |
| 5,688,245 | 11/1997 | Runge | 604/151 |
| 5,702,365 | 12/1997 | King | 604/105 |
| 5,769,821 | 6/1998 | Abrahamson et al. | 604/104 |
| 5,776,111 | 7/1998 | Tesio | 604/264 |
| 5,792,104 | 8/1998 | Speckman et al. | 604/93 |
| 5,797,869 | 8/1998 | Martin et al. | 604/43 |
| 5,807,311 | 9/1998 | Palestrant | 604/28 |
| 5,810,789 | 9/1998 | Powers et al. | 604/280 |
| 5,833,654 | 11/1998 | Powers et al. | 604/93 |

Summary Comparison
Vascular Access Types for Hemodialysis

| Comparative Factor | AV Fistula | PTFE Graft | Percutaneous Catheter Assembly |
|---|---|---|---|
| Average Survival (years) | 3-4 | 2 | 1.5 |
| Major Problem | Patient unsuitability | Clotting | Infection |
| Infection | Low | Moderate | High |
| Clotting | Low | High | Moderate |
| Vein Stenosis | Low | Moderate | Low w/jugular vein<br>High w/subclavian vein |
| Post-dialysis Bleeding | Moderate | Moderate | Low |
| Hospitalization | Moderate | High | Low |
| Blood Flow | High | High | Moderate to high |
| Detrimental Effects with Frequent Use | Low | High | None |
| Placement Before Use | 2-3 months | 2-6 weeks | Immediate |
| Patient Acceptance | Moderate | Moderate | Poor |

FIG. 5

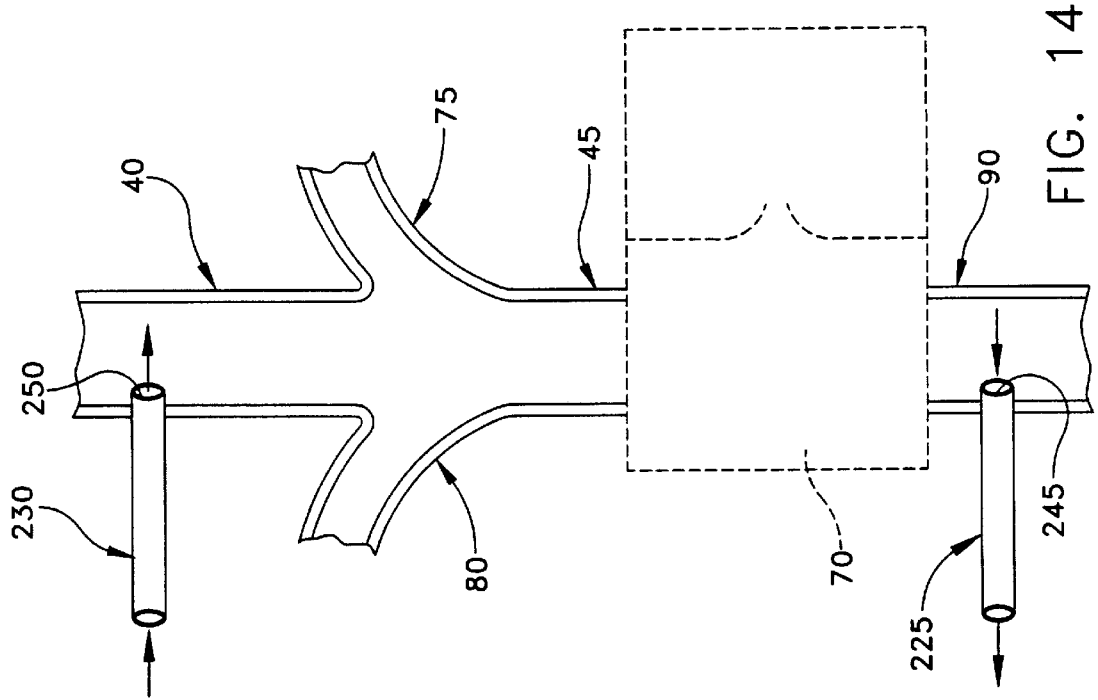
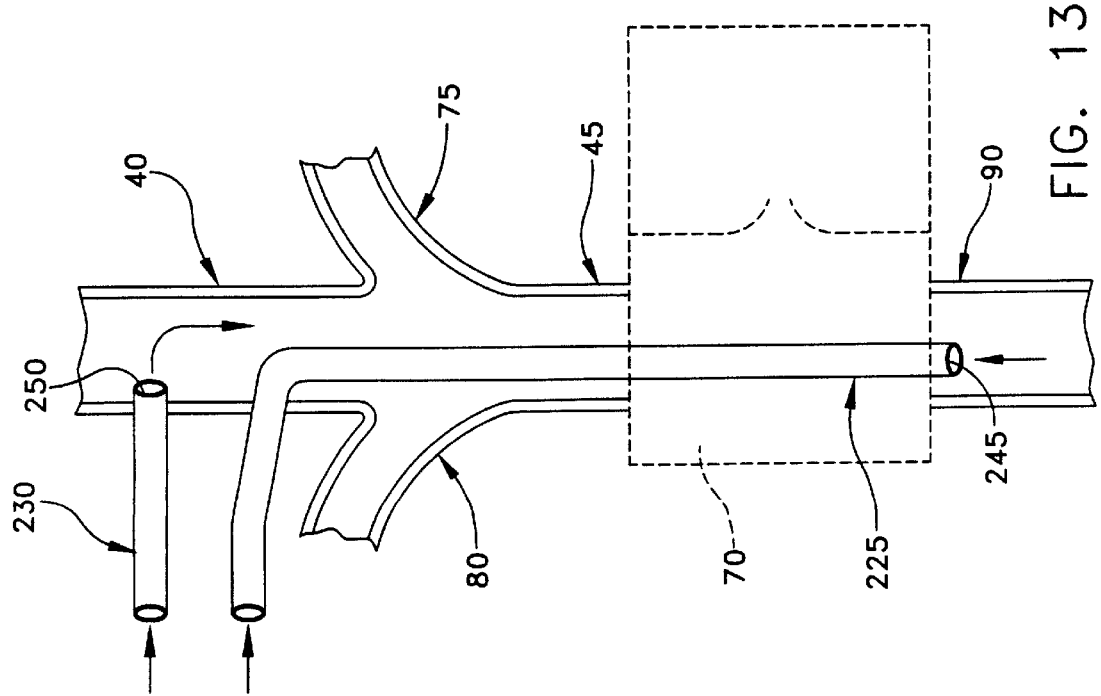

APPARATUS AND METHOD FOR THE DIALYSIS OF BLOOD

FIELD OF THE INVENTION

This invention relates to the dialysis of blood in general, and more particularly to apparatus and methods for use in the same.

BACKGROUND OF THE INVENTION

1. End Stage Renal Disease

A healthy kidney removes toxic wastes and excess water from the blood. In End Stage Renal Disease ("ESRD"), or chronic kidney failure, the kidneys progressively stop performing these essential functions over a long period of time. When the kidneys fail, a patient dies within a short period of time unless that patient receives dialysis treatment for the rest of that patient's life or undergoes transplantation of a healthy, normal kidney. Because few kidneys are available for transplantation, the overwhelming majority of patients with ESRD receive dialysis treatment.

Hemodialysis therapy is an extracorporeal (i.e., outside the body) process which removes toxins and water from a patient's blood. A hemodialysis machine pumps blood from the patient, through a dialyzer, and then back to the patient. The dialyzer removes the toxins and water from the blood by a membrane diffusion principle. Typically, a patient with chronic kidney disease requires hemodialysis three times per week for 3–6 hours per session. Removing blood from the body requires a vascular access to the patient's blood system. This vascular access can be accomplished by surgically modifying the patient's own blood vessels or attaching an artificial device to the vessels. If the vascular access site is entirely beneath the skin, the skin and the vascular site must be punctured by a needle attached to blood tubing. This needle and tubing is typically called a "set".

This vascular access must remain patent (i.e., unblocked) and free from medical complications to enable dialysis to take place. It must allow blood to flow to the machine at a sufficiently high rate to permit dialysis to take place efficiently. And it should allow the patient to carry on a normal life.

2. Hemodialysis Vascular Access

A. Vascular Access—A Major Medical Need

Vascular access is widely called the "Achilles heel of dialysis" because high morbidity and mortality among dialysis patients is associated with complications of vascular access. Vascular access complications are believed to be the single greatest cause of morbidity and to account for approximately one-fourth of all admissions and hospitalization days in the hemodialysis population.

The financial impact to the health care system of these vascular access problems is enormous. By way of illustration, an analysis of the International Classification of Diseases (ICD-9) codes for the U.S. for 1993 showed over 91,000 procedures for the three codes dealing with (1) "Revise Renal Dialysis Shunt", (2) "Remove Renal Dialysis Shunt", and (3) "Complications of Renal Dialysis Device". More than 450,000 days of hospital stay days were involved for just these three codes alone. Clearly, the complications of the current methods of vascular access are costly, whether measured individually for a single event or aggregately for the whole patient population.

Thus, the need for improved vascular access is great.

B. Three Major Methods of Vascular Access

The major advances in vascular access for hemodialysis are listed below:

| | Year |
|---|---|
| Scribner shunt | 1959 |
| AV (arterio-venous) fistula | 1966 |
| Polytetrafluoroethylene (PTFE) graft | 1977 |
| Percutaneous catheter assembly implanted in jugular vein | 1983 |

1. The Scribner Shunt

The Scribner shunt was the breakthrough percutaneous device which enabled patients with chronic kidney disease to be treated with the primitive, already-existing hemodialysis machines. The Scribner shunt suffered from major infection and clotting problems and is no longer used.

2. The AV (Arterio-Venous) Fistula

The first of the three major methods of permanent vascular access currently in use is the native AV (arterio-venous) fistula. The AV fistula is a surgical construct connecting a patient's major artery to a major vein subcutaneously in the arm. With this new blood flow path, most blood will bypass the high flow resistance of the downstream capillary bed, thereby producing a dramatic increase in the blood flow rate through the fistula. Furthermore, although it is not medically feasible to repeatedly puncture an artery, formation of the fistula "arterializes" the vein. The arterialized vein can be punctured repeatedly, and the high blood flow permits high efficiency hemodialysis to occur. Two fistula needles, connected to blood tubing leading to and from the hemodialysis machine, are used to puncture the skin to gain access to the arterialized vein. Blood is withdrawn from the arterial side of the vein, passes through the machine, where it is cleansed, and returns to the venous side of the access.

3. Polytetrafluoroethylene (PTFE) Graft

The PTFE graft is an artificial, tubular, vascular graft made from polytetrafluoroethylene, a Teflon-type material. Implanted in a surgical procedure, the graft 5 (see FIG. 1) connects an artery 10 to a vein 15 in the arm, forming a bypass which can be punctured by fistula needle sets in the same way a normal AV fistula is accessed.

4. Percutaneous Catheter Assembly Implanted in Jugular Vein

The third method of vascular access for hemodialysis is a central venous percutaneous catheter assembly inserted into a major vein, such as the femoral, subclavian or jugular vein. For long term maintenance dialysis, the jugular vein is the preferred insertion site. These catheter assemblies are percutaneous, with one end external to the body and the other end dwelling in either the superior vena cava or the right atrium of the heart. The external portion of these catheter assemblies has connectors permitting attachment of blood sets leading to and from the hemodialysis machine.

FIGS. 2 and 3 show the traditional manner of positioning a central venous percutaneous catheter assembly 20 within the body. More particularly, percutaneous catheter assembly 20 generally comprises a catheter portion 21 comprising a catheter element 22, and a connector portion 24 comprising an extracorporeal connector element 25. The assembly's extracorporeal connector element 25 is disposed against the chest 30 of the patient, and the distal end 35 of catheter element 22 is passed into the patient's internal jugular vein 40 (FIG. 3) and then down into the patient's superior vena cava 45. More particularly, the distal end 35 of catheter element 22 is positioned within the patient's superior vena cava 45 such that the mouth 50 of suction line 55, and the mouth 60 of return line 65, are both located between the patient's right atrium 70 and the patient's left subclavia vein 75 and right subclavia vein 80. In this respect it is to be appreciated that, since mouth 60 of return line 65 is located distal to mouth 50 of suction line 55, mouth 60 of return line 65 will be located closer to right atrium 70 than is mouth 50 of suction line 55. Thus, mouth 60 of return line 65 is located downstream of mouth 50 of suction line 55. The percutaneous catheter assembly 20 is then left in this position relative to the body, waiting to be used during an active dialysis session.

When hemodialysis is to be performed on the patient, the assembly's extracorporeal connector element 25 is appropriately connected to a dialysis machine (not shown), i.e., suction line 55 is connected to the input port (i.e., the suction port) of the dialysis machine, and return line 65 is connected to the output port (i.e., the return port) of the dialysis machine. The dialysis machine is then activated (i.e., the dialysis machine's blood pump is turned on and the flow rate set), whereupon the dialysis machine will withdraw relatively "dirty" blood from the patient through suction line 55 and return relatively "clean" blood to the patient through return line 65. In this respect it is to be appreciated that, inasmuch as mouth 50 of suction line 55 is positioned upstream from mouth 60 of return line 65, the possibility of a hemodialysis "short circuit" (i.e., of suction line 55 collecting the relatively clean blood being returned to the patient's body by return line 65) will be reduced. In practice, it has generally been found desirable to separate the assembly's two mouths 50 and 60 by a distance of about 2 inches or so in order to avoid such undesired blood recirculation.

In some prior art applications, the distal end 35 of catheter element 22 may be positioned in the patient's right atrium 70 rather than in the patient's superior vena cava 45.

In one prior art construction, and looking now at FIG. 4, the construction of the distal end 35 of catheter element 22 is modified from that shown in FIG. 3. More particularly, in this alternative construction, the locations of the mouths 50 and 60 are reversed from that shown in FIG. 3, i.e., so that suction mouth 50 is disposed distal to return mouth 60. However, this design has not been favored, inasmuch as it presents the apparent risk of a hemodialysis "short circuit", i.e., where suction line 55 collects a substantial portion of the just-cleaned blood being returned to the patient's body by return line 65.

C. Benefits and Limitations of Each Method

FIG. 5 is a summary comparison of the benefits and limitations of each of the three currently-used major methods of hemodialysis vascular access.

1. Benefits and Limitations—the Native AV Fistula

The "gold standard" for vascular access is the native AV fistula. Because of its comparatively longer survival time and relatively lower level of major problems, it is the widely preferred choice of nephrologists. However, data from the 1997 U.S. Renal Data System Report indicates that only about 18% of all hemodialysis patients currently get a native AV fistula, while about 50% receive a PTFE graft and about 32% receive a percutaneous catheter assembly after two months of starting hemodialysis therapy.

The main reason that the AV fistula is not widely used is that the surgically-created AV fistula must "mature". Maturation occurs when high pressure and high blood flow from the connected artery expand the downstream system of veins to which it is surgically connected. Surgeons have found that successful AV fistula maturation is not possible in most patients because of the greatly increasing number of diabetic and older hemodialysis patients who have cardiovascular disease which prevents the maturation. Since surgeons have failed so often to achieve fistula maturation after performing the costly AV fistula surgery, they often no longer even try.

The other reason that AV fistulas are seldom used is that, even when fistula surgery is successful, maturation of the fistula generally takes approximately one to three months. Since about half of all prospective patients present with an immediate and urgent need to start hemodialysis, they cannot wait for AV fistula maturation to occur. They must undergo costly temporary procedures inserting percutaneous catheter assemblies to enable dialysis to take place.

2. Benefits and Limitations—the PTFE Graft

Given that AV fistulas are largely not possible, a PTFE vascular graft is implanted into the overwhelming majority of hemodialysis patients because, in spite of the relatively severe limitations to the PTFE graft, there is simply no better alternative.

The major disadvantages of the PTFE graft are stenosis (i.e., closing of the lumen) and thrombosis (i.e., clotting), both of which block the flow of blood. This dysfunction occurs in almost all graft patients several times in their lives and, because it interferes with life-sustaining dialysis, must be corrected quickly. Interventional procedures include angioplasty to open the stenosis and infusion of thrombolytic agents such as urokinase to dissolve the clots. Clinical studies report that the mean time of the operational use of the graft progressively decreases after each such corrective procedure until the operational time is so short that the surgeon decides to replace the graft. The survival time of the graft, including all repairs necessary to maintain its function, currently averages only about two years.

Medical interventions to maintain PTFE grafts and treatment for patient complications are expensive. Furthermore, declotting is required every 9 months or so on average. Also, because only three sites exist in each arm for placement of the graft, current practice is to perform additional screening procedures in an attempt to extend the survival time of the graft. These additional procedures add cost and inconvenience but have yet to significantly improve upon the mean time between interventional repair, although they may improve graft survival life.

PTFE grafts are structurally weakened, and the flow boundary is impaired, by the frequent (i.e., six times per week) puncturing with large gauge fistula needles. This degradation can lead to several complications and dysfunction, including post-dialysis bleeding, aneurysms and increased stenosis and thrombosis causing flow obstructions. Furthermore, a rough surface on the graft's exterior can become a place for bacteria to be protected from the body's defenses and antibiotic treatment. This further necessitates intervention and increases costs for access maintenance.

A PTFE graft (as well as an AV fistula) can also cause death in patients with heart problems. This is because the graft allows blood to bypass the lower circulation in the arm, which greatly reduces blood flow resistance in the arm as well as the whole body. The heart, which is a pump, recognizes lower system flow resistance and automatically adjusts to a higher cardiac output (i.e., a higher blood flow rate through the heart). Patients Who are older and with weak hearts may not adapt to this and can incur a cardiac arrest. Physicians considering this possibility currently screen out about 6% of all hemodialysis patients from acquiring a graft or fistula.

An additional disadvantage to PTFE grafts is that they take time to mature before they can be used. About 50% of patients present with a need for immediate hemodialysis and the surgeon must place a temporary access (i.e., a central venous percutaneous catheter assembly) for immediate use while the graft is maturing. This usually takes several weeks.

The cost to place an additional vascular access for hemodialysis further consumes medical resources.

Another limitation of PTFE grafts is that the Teflon-type material does not seal as well as a native vein after removal of the fistula needle. Also, pressure in the graft is higher than venous pressure. This typically results in blood spurting out of the hole created by the needle puncture upon withdrawal of the needle. Achieving hemostasis requires that the puncture site be held with a finger or other means for a considerable period of time (usually 10 to 20 minutes) while maintaining pressure until the blood clots and bleeding stops.

3. Benefits and Limitations—Central Venous Percutaneous Catheter Assembly

The third method of permanent vascular access is a percutaneous central venous catheter assembly inserted through the skin into a major vein, with the distal tips of the catheter element advanced into the right atrium of the heart or the superior vena cava, a major vein leading into the right atrium. Percutaneous catheter assemblies have been used in hemodialysis since the early 1960's but were for many years considered "temporary" vascular access because of major infection and stenosis problems. Because they can be easily and quickly inserted, they were used only when emergency vascular access was needed to permit hemodialysis. For many years, potentially life-threatening infection complications were so great that the percutaneous catheter assemblies were withdrawn after each dialysis session and re-inserted before the next session so as to minimize the risk of infection.

Two important developments were made in the 1980's that have led some nephrologists to consider percutaneous catheter assemblies as "permanent" vascular access. The most important of these developments was a 1983 paper reporting the insertion of percutaneous catheter assemblies into the jugular vein rather than the subclavian vein. Jugular vein insertion essentially eliminated the problem of subclavian vein stenosis associated with up to 50% of subclavian vein catheter insertions. Subclavian vein stenosis not only blocks blood flow, making it impossible to conduct hemodialysis, but also, catastrophically, can destroy all potential vascular access sites in one or both arms. Given the short survival time for all vascular access sites, preservation of vascular access sites is a major imperative of artificial kidney treatment.

The second major development was the attachment of a dacron "cuff" to the assembly's catheter element, near the proximal end, under the skin, about an inch from the incision site where the assembly exits the body. This cuff permits tissue in-growth to occur which fastens the catheter element to the tissue, thereby reducing movement of the percutaneous catheter assembly at the incision site as well as in the blood vessel. In addition, such tissue in-growth is believed by many to retard bacterial travel along the outer surface of the percutaneous catheter assembly, although it does not prevent it entirely. While numerous reports suggest that the cuff has reduced the infection rate, infections remain a major problem with the use of cuffed percutaneous catheter assemblies.

Because of these developments, a series of papers published in the 1990's reported positively on the long term survival of percutaneous catheter assemblies, thereby permitting their use in "permanent" vascular access. It is anticipated, however, that PTFE grafts will continue to be preferred to percutaneous catheter assemblies because PTFE grafts permit longer use without intervention (see FIG. 5).

The principal factor limiting percutaneous catheter assembly survival, and time without incidents requiring medical intervention, is infection, which continues to occur at a high rate. Clinical experience indicates that about 82% of all percutaneous catheter assembly failures and complications are attributable to infection.

To make percutaneous catheter assemblies a widely accepted form of permanent vascular access, one must resolve infection complications. However, as long as the percutaneous catheter assembly breaks through the skin, which is the body's barrier to infection, the pathway for bacteria from outside the body to the subcutaneous tissue exists. It should be noted that the PTFE graft, which is entirely subcutaneous, has a much lower rate of infection than the percutaneous catheter assembly. With a PTFE graft, the skin and the graft are in contact only with sterile fistula needles during the dialysis session.

Another limitation to percutaneous catheter assemblies compared to PTFE grafts is that, historically, permissible blood flow rates are much lower with percutaneous catheter assemblies because the pressure drop through the percutaneous catheter assembly is higher than through a PTFE graft. As a result, it has been difficult to conduct the high efficiency (i.e., the short time) dialysis protocols used in for-profit dialysis centers with percutaneous catheter assembly access.

Percutaneous catheter assemblies also have problems with flow obstructions. More particularly, when a percutaneous catheter is left in the body for a significant period of time, fibrin sheaths can form about the distal end of the catheter element, and these fibrin sheaths can obstruct the flow of blood into the mouth of the suction line. In addition, blood clots can also obstruct the flow of blood into the mouth of the catheter assembly's suction line. Furthermore, if the distal tip of the catheter element engages the side wall of the host blood vessel, the catheter element can irritate the side wall of that blood vessel, causing tissue to grow about the distal tip of the catheter element. This tissue can also obstruct the flow of blood into the mouth of the catheter assembly's suction line.

Also, at high dialysis flow rates, suction line 55 of catheter element 22 can sometimes draw the side wall 85 (FIG. 6) of superior vena cava 45 inward, toward mouth 50 of suction line 55, due to its aggressive suction action. When this occurs, side wall 85 may interfere with the flow of blood into mouth 50 of suction line 55. In addition, this inward movement of side wall 85 also acts to narrow the internal diameter of superior vena cava 45, thereby reducing the rate at which blood may be withdrawn from, or returned to, that host blood vessel. Both of these effects can reduce the throughput of the dialysis machine, thereby increasing the patient's dialysis time and reducing the total number of patients who may be treated with that particular dialysis machine. On the other hand, if the level of suction is lowered so as to reduce the possibility of drawing side wall 85 into mouth 50 of suction line 55, then the overall flow of blood through the percutaneous catheter assembly will also be reduced, thereby again decreasing the total throughput of the dialysis machine.

Also, patient acceptance of percutaneous catheter assemblies has always been low due to self-image concerns and limitations on life style. The percutaneous catheter assembly exiting the body from the neck or chest is a visible reminder (both to the patient and others) of the patient's hemodialysis-machine-dependent illness. Patients also tend to dislike percutaneous catheter assemblies because bathing and other normal activities generally have to be restricted to protect the percutaneous catheter assembly.

In addition to the foregoing, it has also been found that air embolisms can be accidentally introduced into the patient when using percutaneous catheter assemblies.

Also, it has been found that the percutaneous catheter assembly's extracorporeal connector element can be damaged by undesired contact during the periods between dialysis sessions.

Percutaneous catheter assemblies do have certain inherent advantages, however. For one thing, they can be quickly, easily, and inexpensively inserted into the patient. In addition, there is no detrimental physical effect to the device from frequent use because, unlike PTFE grafts, it is not necessary to repeatedly puncture the device with large gauge fistula needles. Furthermore, there are few post-dialysis bleeding problems at the access site because the blood conduit is not punctured with fistula needles.

D. Subcutaneous Infusion Port Assemblies

Subcutaneous infusion port assemblies are currently in use in the field of oncology, to facilitate the repeated and regular delivery of chemotherapy agents to cancer patients. Such subcutaneous infusion port assemblies generally comprise a needle-receiving septum and a fluid line extending out of the needle-receiving septum. The subcutaneous infusion port assembly is surgically implanted in the patient's body on a semi-permanent basis, with the needle-receiving septum being disposed subcutaneously in the chest area of the patient, and with the fluid line leading from the needle-receiving septum into the vascular system of the patient. During a chemotherapy session, medical personnel pass a needle through the skin of the patient and into fluid engagement with the subcutaneous needle-receiving septum. This arrangement allows the desired chemotherapy agents to be delivered from a location outside the body into the subcutaneous needle-receiving septum, whereupon the chemotherapy agents can flow into the patient's vascular system so as to effect the desired treatment.

Only one known prior art attempt has been made to use chemotherapy infusion port assemblies in hemodialysis applications. This attempt was not satisfactory, for a variety of reasons.

OBJECTS OF THE INVENTION

Accordingly, one object of the present invention is to provide improved apparatus for use in the dialysis of blood.

Another object of the present invention is to provide improved apparatus for use in the dialysis of blood, wherein use of the improved apparatus will yield increased operating time between clotting episodes, thereby leading to lower overall medical costs by reducing patient hospitalizations and surgical procedures.

And another object of the present invention is to provide improved apparatus for use in the dialysis of blood, wherein use of the improved apparatus will result in reduced infection problems.

Still another object of the present invention is to provide improved apparatus for use in the dialysis of blood, wherein use of the improved apparatus will not tend to increase cardiac output, which in turn tends to place increased stress on the heart of the patient.

Yet another object of the present invention is to provide improved apparatus for use in the dialysis of blood, wherein use of the improved apparatus will not require significant maturation time between the time the apparatus is placed in the body and the time use of the apparatus may commence.

And still another object of the present invention is to provide improved apparatus for use in the dialysis of blood, wherein the improved apparatus will be better accepted by the patient.

And yet another object of the present invention is to provide improved apparatus for use in the dialysis of blood, wherein use of the improved apparatus will not result in post-dialysis bleeding and/or intra-dialysis bleeding.

Another object of the present invention is to provide improved apparatus for use in the dialysis of blood, wherein use of the improved apparatus will result in less flow obstruction problems.

Still another object of the present invention is to provide improved apparatus for use in the dialysis of blood, wherein use of the improved apparatus will result in less air embolism problems.

Yet another object of the present invention is to provide improved apparatus for use in the dialysis of blood, wherein the improved apparatus will be less likely to be damaged by undesired contact during the periods between dialysis sessions.

And another object of the present invention is to provide improved apparatus for use in the dialysis of blood, wherein the improved apparatus permits dialysis to be conducted with higher blood flow rates.

Another object of the present invention is to provide an improved method for the dialysis of blood.

SUMMARY OF THE INVENTION

These and other objects are achieved through the provision and use of the present invention, which comprises an improved apparatus and method for the dialysis of blood.

In one form of the invention, the improved apparatus for the dialysis of blood comprises a subcutaneous port and catheter assembly for use in the dialysis of the blood of a patient, the assembly comprising a connector portion and a catheter portion; the connector portion comprising a subcutaneous port element adapted for implantation within the body of the patient, the subcutaneous port element comprising an inlet adapted for communication with a percutaneous needle connected to the output port of a dialysis machine, and an outlet adapted for communication with a percutaneous needle connected to the input port of a dialysis machine; and the catheter portion comprising a catheter element comprising: a suction line having a proximal end and a distal end, the proximal end of the suction line being connected to the subcutaneous port element and in communication with the outlet, and the distal end of the suction line terminating in a suction line mouth; and a return line having a proximal end and a distal end, the proximal end of the return line being connected to the subcutaneous port element and in communication with the inlet, and the distal end of the return line terminating in a return line mouth; the suction line and the return line being adapted for disposition within the body of the patient so that the suction line mouth and the return line mouth are both disposed in the vascular system of the patient, the suction line mouth and the return line mouth being disposed different distances from the connector portion.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition within the body of the patient so that the suction line mouth and the return line mouth are both disposed in the vascular system of the patient; the suction line having a length facilitating the disposition of the suction line mouth in a first portion of the vascular system of the patient, the first portion being selected from a group of portions consisting of (1) a right atrium portion, and (2) an inferior vena cava portion; and the return line having a length facilitating the disposition of the return line mouth in a second portion of the vascular system of the patient, the second portion being selected from a group of portions consisting of (1) an internal jugular vein portion, and (2) a superior vena cava portion.

In another form of the invention, the improved apparatus for the dialysis of blood comprises a connector portion and a catheter portion; the connector portion comprising an inlet adapted for communication with a line connected to the output port of a dialysis machine; and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition within the body of the patient so that the suction line mouth and the return line mouth are both disposed in the vascular system of the patient; the suction line having a length facilitating the disposition of the suction line mouth in a first portion of the vascular system of the patient, the first portion being selected from a group of portions consisting of (1) a right atrium portion, (2) an inferior vena cava portion, and (3) a superior vena cava portion; and the return line having a length facilitating the disposition of the return line mouth in the right ventricle of the heart.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the return line comprises a flange adjacent the return line mouth, and the apparatus further comprises a locking collar for capturing a wall of the vascular system of the patient between the flange and the locking collar.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the apparatus further comprises a support member interconnecting the distal end of the suction line and an inside wall of the vascular system of the patient so as to position the suction line mouth substantially centrally of the inside wall of the vascular system of the patient.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the distal end of the suction line and the distal end of the return line includes a relatively stiff portion to help maintain that line in a selected position within the vascular system of the patient.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the distal end of the suction line and the distal end of the return line includes projections extending radially therefrom so as to keep that line's mouth spaced some distance away from an inside wall of the vascular system of the patient.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the central lumen of the suction line and the central lumen of the return line is gradually diametrically increased in a flared manner, with that central lumen having a maximum diameter at that line's distal mouth.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the distal end of the suction line and the distal end of the return line includes at least one side opening adjacent that line's mouth whereby fluid may enter that line even if that line's mouth should be occluded.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the catheter element is constructed so that the suction line mouth is spaced from the return line mouth such that the suction line mouth is further from the connector portion than the return line mouth; and a sleeve having a first portion disposed around an intermediate portion of the suction line and the distal end of the return line, and a second portion disposed around the suction line distally of the return line, the sleeve second portion being integral with and an extension of the sleeve first portion, the sleeve being made of elastic material such that when the apparatus is not in operation, the sleeve second portion contracts around the suction line and blocks off the return line mouth, and when the apparatus is in operation, the sleeve second portion is opened by outflow from the return line mouth.

In another form of the invention, the improved apparatus for the dialysis of blood comprises a subcutaneous port and catheter assembly for use in the dialysis of the blood of a patient, the assembly comprising a connector portion and a catheter portion; the connector portion comprising a subcutaneous port element adapted for implantation within the body of the patient, the subcutaneous port element comprising an inlet adapted for communication with a percutaneous needle connected to the output port of a dialysis machine, and an outlet adapted for communication with a percutaneous needle connected to the input port of a dialysis machine; and the catheter portion comprising a catheter element comprising: a suction line having a proximal end and a distal end, the proximal end of the suction line being connected to the subcutaneous port element and in communication with the outlet, and the distal end of the suction line terminating in a suction line mouth; and a return line having a proximal end and a distal end, the proximal end of the return line being connected to the subcutaneous port element and in communication with the inlet, and the distal end of the return line terminating in a return line mouth; the suction line and the return line being adapted for disposition within the body of the patient so that the suction line mouth and the return line mouth are both disposed in the vascular system of the patient; the return line being formed out of an elastomeric material such that the return line will collapse down when the apparatus is not in use and expand outward when the apparatus is in use.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the central lumen of the suction line and the central lumen of the return line is tapered along its length, with the inner diameter of that line being larger at the proximal end of that line than at the distal end of that line.

In another form of the invention, the improved apparatus for the dialysis of blood comprises a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the catheter element comprises a proximal section and a distal section, the proximal section and the distal section being connected together by a coupling element adapted to be positioned at the point where the catheter element enters the vascular system of the patient. In one preferred form of the invention, the coupling element is formed out of a relatively rigid material, and is preformed in a relatively tight bend radius, so as to avoid kinking problems at the point where the catheter element enters the vascular system of the patient.

In another form of the invention, the improved apparatus for the dialysis of blood comprises a subcutaneous port and catheter assembly for use in the dialysis of the blood of a patient, the assembly comprising a connector portion and a catheter portion; the connector portion comprising a subcutaneous port element adapted for implantation within the body of the patient, the subcutaneous port element comprising an inlet adapted for communication with a percutaneous needle connected to the output port of a dialysis machine, and an outlet adapted for communication with a percutaneous needle connected to the input port of a dialysis machine; and the catheter portion comprising a catheter element comprising: a suction line having a proximal end and a distal end, the proximal end of the suction line being connected to the subcutaneous port element and in communication with the outlet, and the distal end of the suction line terminating in a suction line mouth; and a return line having a proximal end and a distal end, the proximal end of the return line being connected to the subcutaneous port element and in communication with the inlet, and the distal end of the return line terminating in a return line mouth; the suction line and the return line being adapted for disposition within the body of the patient so that the suction line mouth and the return line mouth are both disposed in the vascular system of the patient; at least one of the suction line and the return line incorporating a coiled spring therein such that the line will not kink when the line is subjected to significant bending.

In one form of the invention, the improved method for the dialysis of blood comprises the steps of:

(1) providing a subcutaneous port and catheter assembly for use in the dialysis of the blood of a patient, the assembly comprising a connector portion and a catheter portion; the connector portion comprising a subcutaneous port element adapted for implantation within the body of the patient, the subcutaneous port element comprising an inlet adapted for communication with a percutaneous needle connected to the output port of a dialysis machine, and an outlet adapted for communication with a percutaneous needle connected to the input port of a dialysis machine; and the catheter portion comprising a catheter element comprising: a suction line having a proximal end and a distal end, the proximal end of the suction line being connected to the subcutaneous port element and in communication with the outlet, and the distal end of the suction line terminating in a suction line mouth; and a return line having a proximal end and a distal end, the proximal end of the return line being connected to the subcutaneous port element and in communication with the inlet, and the distal end of the return line terminating in a return line mouth; the suction line and the return line being adapted for disposition within the body of the patient so that the suction line mouth and the return line mouth are both disposed in the vascular system of the patient, the suction line mouth and the return line mouth being disposed different distances from the connector portion;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition within the body of the patient so that the suction line mouth and the return line mouth are both disposed in the vascular system of the patient; the suction line having a length facilitating the disposition of the suction line mouth in a first portion of the vascular system of the patient, the first portion being selected from a group of portions consisting of (1) a right atrium portion, and (2) an inferior vena cava portion; and the return line having a length facilitating the disposition of the return line mouth in a second portion of the vascular system of the patient, the second portion being selected from a group of portions consisting of (1) an internal jugular vein portion, and (2) a superior vena cava portion;

(2) placing the suction line mouth and the return line mouth in the vascular system of the patient so that the suction line mouth is disposed in a first portion of the vascular system of the patient, the first portion being selected from a group of portions consisting of (1) a right atrium portion, and (2) an inferior vena cava portion; and so that the return line is disposed in a second portion of the vascular system of the patient, the second portion being selected from a group of portions consisting of (1) an internal jugular vein portion, and (2) a superior vena cava portion;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition within the body of the patient so that the suction line mouth and the return line mouth are both disposed in the vascular system of the patient; the suction line having a length facilitating the disposition of the suction line mouth in a first portion of the vascular system of the patient, the first portion being selected from a group of portions consisting of (1) a right atrium portion, (2) an inferior vena cava portion, and (3) a superior vena cava portion; and the return line having a length facilitating the disposition of the return line mouth in the right ventricle of the heart;

(2) placing the suction line mouth and the return line mouth in the vascular system of the patient so that the suction line mouth is disposed in a first portion of the vascular system of the patient, the first portion being selected from a group of portions consisting of (1) a right atrium portion, (2) an inferior vena cava portion, and (3) a superior vena cava portion; and so that the return line is disposed in the right ventricle of the heart;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the return line comprises a flange adjacent the return line mouth, and the apparatus further comprises a locking collar for capturing a wall of the vascular system of the patient between the flange and the locking collar;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the apparatus further comprises a support member interconnecting the distal end of the suction line and an inside wall of the vascular system of the patient so as to position the suction line mouth substantially centrally of the inside wall of the vascular system of the patient;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the distal end of the suction line and the distal end of the return line includes a relatively stiff portion to help maintain that line in a selected position within the vascular system of the patient;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the distal end of the suction line and the distal end of the return line includes projections extending radially therefrom so as to keep that line's mouth spaced some distance away from an inside wall of the vascular system of the patient;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the central lumen of the suction line and the central lumen of the return line is gradually diametrically increased in a flared manner, with that central lumen having a maximum diameter at that line's distal mouth;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the distal end of the suction line and the distal end of the return line includes at least one side opening adjacent that line's mouth whereby fluid may enter that line even if that line's mouth should be occluded;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine; and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the catheter element is constructed so that the suction line mouth is spaced from the return line mouth such that the suction line mouth is further from the connector portion than the return line mouth; and a sleeve having a first portion disposed around an intermediate portion of the suction line and the distal end of the return line, and a second portion disposed around the suction line distally of the return line, the sleeve second portion being integral with and an extension of the sleeve first portion, the sleeve being made of elastic material such that when the apparatus is not in operation, the sleeve second portion contracts around the suction line and blocks off the return line mouth, and when the apparatus is in operation, the sleeve second portion is opened by outflow from the return line mouth;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing a subcutaneous port and catheter assembly for use in the dialysis of the blood of a patient, the assembly comprising a connector portion and a catheter portion; the connector portion comprising a subcutaneous port element adapted for implantation within the body of the patient, the subcutaneous port element comprising an inlet adapted for communication with a percutaneous needle connected to the output port of a dialysis machine, and an outlet adapted for communication with a percutaneous needle connected to the input port of a dialysis machine; and the catheter portion comprising a catheter element comprising: a suction line having a proximal end and a distal end, the proximal end of the suction line being connected to the subcutaneous port element and in communication with the outlet, and the distal end of the suction line terminating in a suction line mouth; and a return line having a proximal end and a distal end, the proximal end of the return line being connected to the subcutaneous port element and in communication with the inlet, and the distal end of the return line terminating in a return line mouth; the suction line and the return line being adapted for disposition within the body of the patient so that the suction line mouth and the return line mouth are both disposed in the vascular system of the patient; the return line being formed out of an elastomeric material such that the return line will collapse down when the apparatus is not in use and expand outward when the apparatus is in use;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein at least one of the central lumen of the suction line and the central lumen of the return line is tapered along its length, with the inner diameter of that line being larger at the proximal end of that line than at the distal end of that line;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In another form of the invention, the improved method for the dialysis of blood comprises the steps of:

(1) providing apparatus for use in the dialysis of the blood of a patient, the apparatus comprising a connector portion and a catheter portion; the connector portion comprising an inlet adapted for communication with a line connected to the output port of a dialysis machine, and an outlet adapted for communication with a line connected to the input port of a dialysis machine; and the catheter portion comprising a catheter element comprising: a suction line having a proximal end and a distal end, the proximal end of the suction line being connected to the connector portion and in communication with the outlet, and the distal end of the suction line terminating in a suction line mouth; and a return line having a proximal end and a distal end, the proximal end of the return line being connected to the connector portion and in communication with the inlet, and the distal end of the return line terminating in a return line mouth; the suction line and the return line being adapted for disposition relative to the body of the patient so that the suction line mouth and the return line mouth are both disposed in the vascular system of the patient; and further wherein the catheter element comprises a proximal section and a distal section, the proximal section and the distal section being connected together by a coupling element adapted to be positioned at the point where the catheter element enters the vascular system of the patient;

(2) placing the suction line mouth and the return line mouth in the vascular system of the patient;

(3) connecting the outlet to the input port of a dialysis machine, and connecting the inlet to the output port of a dialysis machine; and (4) operating the dialysis machine.

In one preferred form of the invention, the coupling element is formed out of a relatively rigid material, and is preformed in a relatively tight bend radius, so as to avoid kinking problems at the point where the catheter element enters the vascular system of the patient.

In another form of the invention, the improved method for the dialysis of blood comprises the steps of:

(1) providing a subcutaneous port and catheter assembly for use in the dialysis of the blood of a patient, the assembly comprising a connector portion and a catheter portion; the connector portion comprising a subcutaneous port element adapted for implantation within the body of the patient, the subcutaneous port element comprising an inlet adapted for communication with a percutaneous needle connected to the output port of a dialysis machine, and an outlet adapted for communication with a percutaneous needle connected to the input port of a dialysis machine; and the catheter portion comprising a catheter element comprising: a suction line having a proximal end and a distal end, the proximal end of the suction line being connected to the subcutaneous port element and in communication with the outlet, and the distal end of the suction line terminating in a suction line mouth; and a return line having a proximal end and a distal end, the proximal end of the return line being connected to the subcutaneous port element and in communication with the inlet, and the distal end of the return line terminating in a return line mouth; the suction line and the return line being adapted for disposition within the body of the patient so that the suction line mouth and the return line mouth are both disposed in the vascular system of the patient; at least one of the suction line and the return line incorporating a coiled spring therein such that the line will not kink when the line is subjected to significant bending;

(2) placing the suction line mouth and the return line mouth in the vascular system of the patient;

(3) connecting the outlet to the input port of a dialysis machine, arid connecting the inlet to the output port of a dialysis machine; and (4) operating the dialysis machine.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein:

FIG. 5 is a chart showing a summary comparison of different types of vascular access for hemodialysis treatment;

FIGS. 11–14 and 14A are schematic views showing alternative methods for installing the novel subcutaneous port and catheter assembly of FIG. 9 in a human body;

DETAILED DESCRIPTION OF THE PREFERRED EMBODIMENTS

Figure 7:
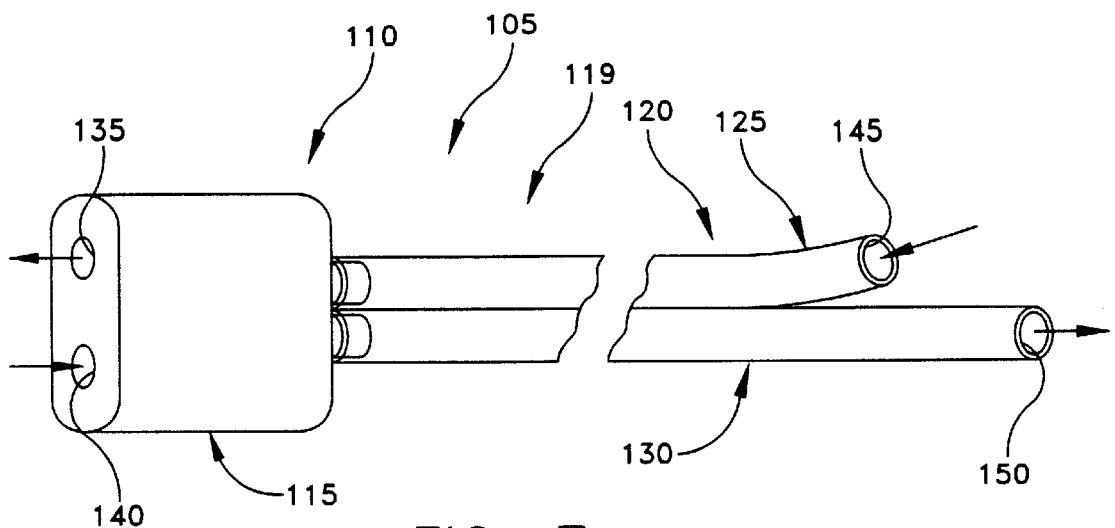
FIG. 7 is a novel hemodialysis subcutaneous port and catheter assembly formed in accordance with the present invention.

Looking next at FIG. 7, there is shown a novel hemodialysis subcutaneous port and catheter assembly 105 formed in accordance with the present invention. Subcutaneous port and catheter assembly 105 generally comprises a connector portion 110 comprising a subcutaneous port element 115, and a catheter portion 119 comprising a catheter element 120. Catheter element 120 is turn comprises a suction line 125 and a return line 130. Subcutaneous port element 115 includes a needle port 135 which is connected to suction line 125, and a needle port 140 which is connected to return line 130. The distal end of suction line 125 terminates in a mouth 145, and the distal end of return line 130 terminates in a mouth 150. It is to be appreciated that in subcutaneous port and catheter assembly 105, mouth 145 of suction line 125 is spaced proximally from mouth 150 of return line 130, for reasons which will hereinafter be discussed.

In other words, mouth 150 of return line 130 is located distal to mouth 145 of suction line 125.

Figure 8:
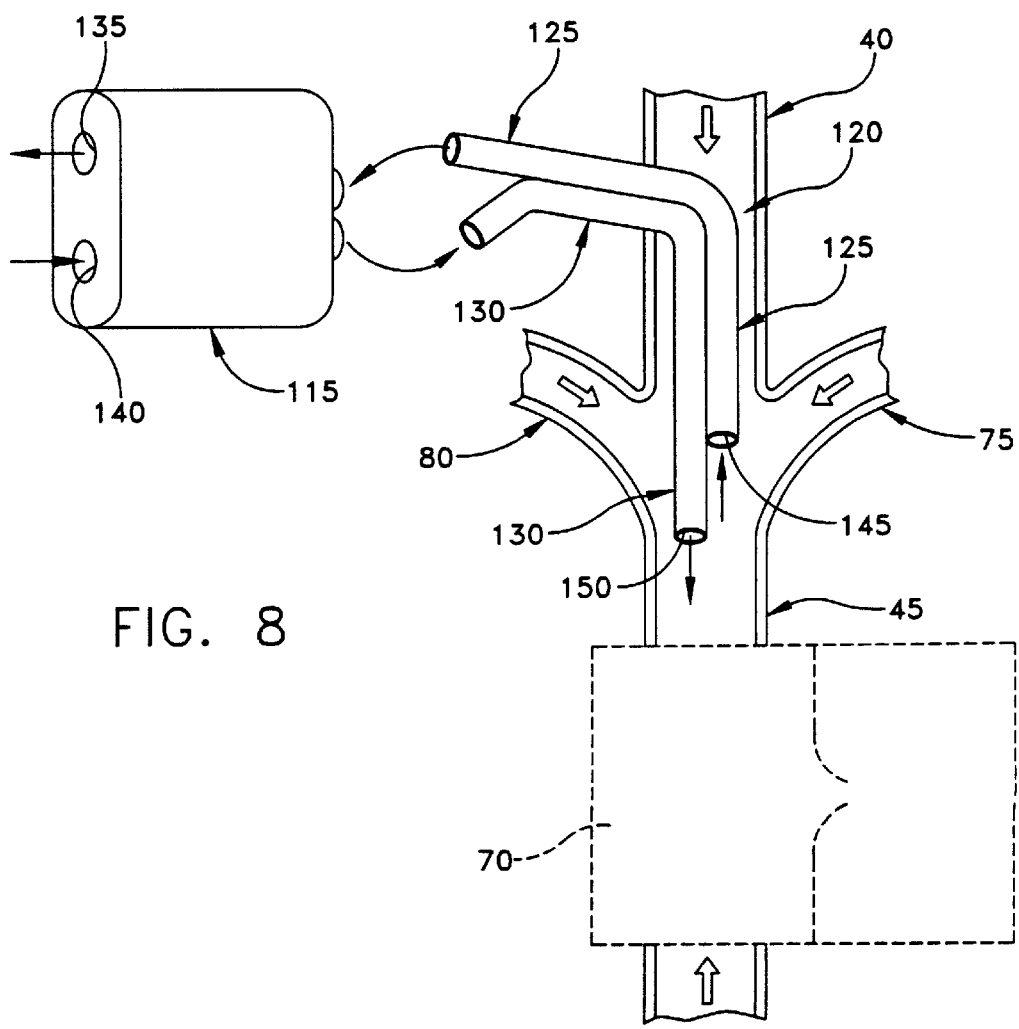
FIG. 8 is a schematic view showing the novel subcutaneous port and catheter assembly of FIG. 7 installed in a human body.

FIG. 8 shows subcutaneous port and catheter assembly 105 positioned within the body. More particularly, the assembly's port element 115 is disposed under the skin of the patient (e.g., in the chest area of the patient), and the assembly's catheter element 120 is passed into the patient's internal jugular vein 40 and then down into the patient's superior vena cava 45. More particularly, the distal end of the assembly's catheter element 120 is positioned within the patient's superior vena cava 45 such that mouth 145 of suction line 125, and mouth 150 of return line 130, are both located approximately between the patient's right atrium 70 and the patient's left subclavia vein 75 and right subclavia vein 80. In this respect it is to be appreciated that, since mouth 150 of return line 130 is located distal to mouth 145 of suction line 125, mouth 150 of return line 130 will be located closer to right atrium 70 than is mouth 145 of suction line 125. Thus, mouth 150 of return line 130 is located downstream of mouth 145 of suction line 125. The assembly is then left in this position within the body, waiting to be used during an active dialysis session.

When hemodialysis is to be performed on the patient, the assembly's subcutaneous port element 115 is appropriately connected to a dialysis machine, i.e., needle port 135 is connected to the input port (i.e., the suction port) of the dialysis machine with an appropriate percutaneous needle (not shown), and the assembly's needle port 140 is connected to the output port (i.e., the return port) of the dialysis machine with an appropriate percutaneous needle (not shown). The dialysis machine is then activated, whereupon it will withdraw relatively "dirty" blood from the patient through suction line 125 and return relatively "clean" blood to the patient through return line 130. In this respect it is to be appreciated that, by virtue of the fact that mouth 145 of suction line 125 is positioned 30 upstream from mouth 150 of return line 130, the possibility of a hemodialysis "short circuit" (i.e., of suction line 125 collecting the relatively clean blood being returned to the patient's body by return line 130) will be reduced. In practice, it has generally been found desirable to separate mouths 145 and 150 of the assembly by a distance of about 2 inches or so in order to avoid such undesired blood recirculation.

Figure 9:
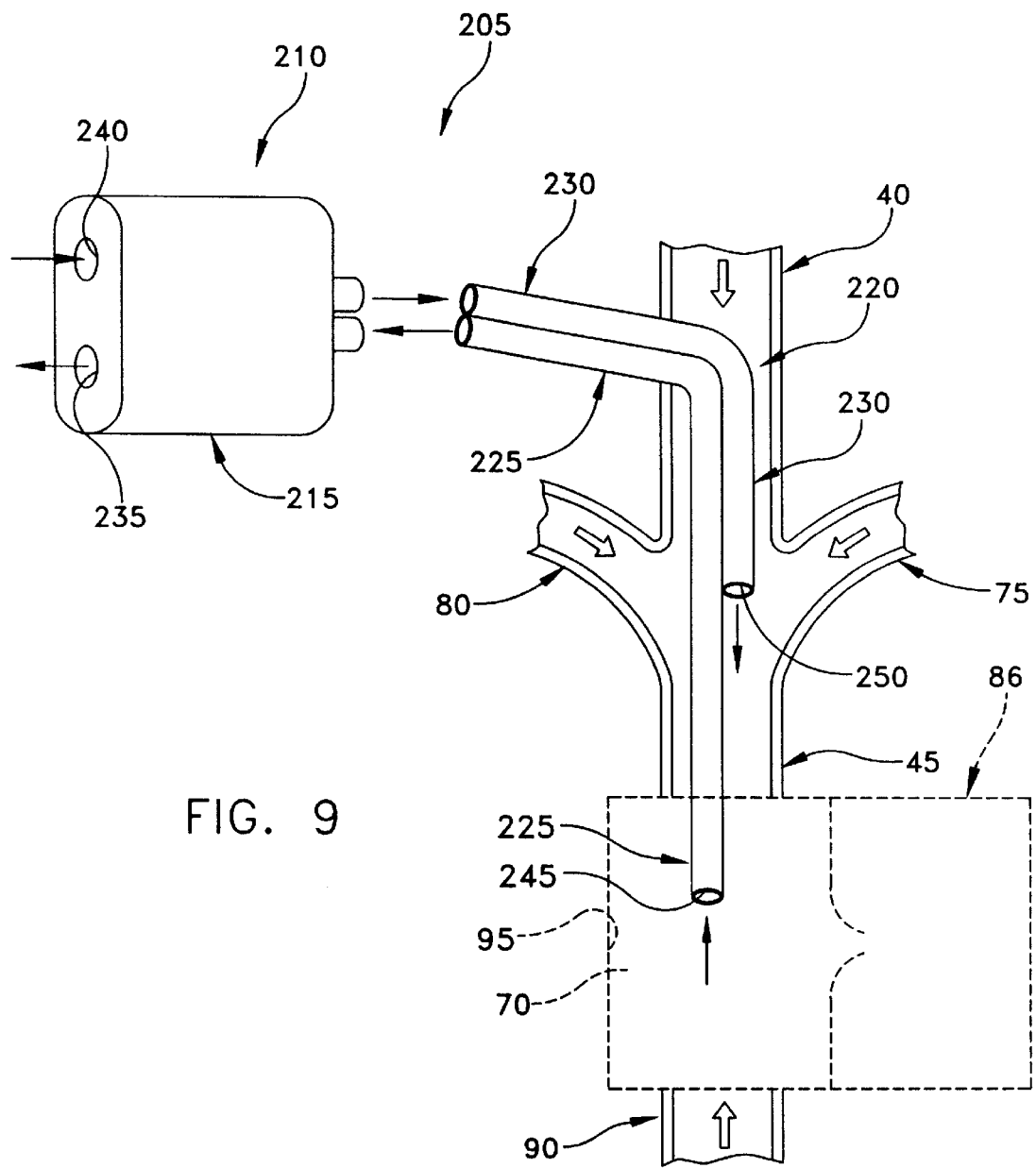
FIG. 9 is a schematic view showing another novel form of subcutaneous port and catheter assembly installed in a human body.

Looking next at FIG. 9, a novel subcutaneous port and catheter assembly 205 is shown. Assembly 205 is substantially the same as assembly 105 discussed above, except that the catheter element 220 of assembly 205 is configured so that the mouth 245 of suction line 225 is disposed distal to mouth 250 of return line 230, for reasons which will hereinafter be made clear. This is in direct contrast to assembly 105 discussed above, in which mouth 145 of suction line 125 is disposed proximal to mouth 150 of return line 130. Furthermore, with assembly 205, mouth 245 of suction line 225 is located a significant anatomical distance from mouth 250 of return line 230, for reasons which will also hereinafter be made clear.

In accordance with one form of the present invention, in use, the assembly's subcutaneous port element 215 is disposed under the skin of the patient, and its catheter element 220 is passed into the patient's internal jugular vein 40 and then down the patient's superior vena cava 45. Return line 230 is positioned so that its mouth 250 remains in superior vena cava 45, either above or below left subclavia vein 75 and right subclavia vein 80. At the same time, suction line 225 is sized and positioned so that its mouth 245 extends significantly further down superior vena cava 45 than mouth 250 of return line 230. Preferably suction line 225 is sized and positioned so that its mouth 245 extends down into the patient's right atrium 70. Assembly 205 is then left in this position within the body, waiting to be used during an active dialysis session.

When dialysis is to be performed on the patient, the assembly's needle port 235 is connected to the input port (i.e., the suction port) of a dialysis machine (not shown) with an appropriate percutaneous needle (not shown), and the catheter's needle port 240 is connected to the output port (i.e., the return port) of the dialysis machine with an appropriate percutaneous needle (not shown). The dialysis machine is then activated, whereupon it will withdraw relatively "dirty" blood from the patient through suction line 225 and return relatively "clean" blood to the patient through return line 230. In this respect it is to be appreciated that, by positioning mouth 245 of suction line 225 in the patient's right atrium 70 while mouth 250 of return line 230 is positioned in the patient's superior vena cava 45, the possibility of a hemodialysis "short circuit" (i.e., of suction line 225 collecting the relatively clean blood being returned to the patient's body by return line 230 ) will be reduced. This is true even though mouth 245 of suction line 225 is disposed distal to mouth 250 of return line 230. In fact, inasmuch as the blood being returned to heart 86 (FIG. 9) by inferior vena cava 90 is somewhat "dirtier" than the blood being returned to heart 86 by superior vena cava 45, dialysis of the patient will be somewhat more efficient than previous modes of practice.

Furthermore, inasmuch as mouth 245 of suction line 225 is disposed within the interior of the patient's right atrium 70, and inasmuch as right atrium 70 has a relatively large volume, there is relatively little likelihood that suction from suction line 225 will cause a side wall 95 of right atrium 70 to move toward mouth 245 of suction line 225. This is due to several factors. For one thing, the volume of the patient's right atrium 70 is relatively large compared to the size of mouth 245 of suction line 225, such that mouth 245 of suction line 225 will generally tend to reside relatively far from any adjacent vascular side walls. For another thing, the volumetric blood flow in right atrium 70 is approximately three times higher than the volumetric blood flow in superior vena cava 45, so that the likelihood of causing the collapse of the blood conduit is relatively remote. Also, the right atrium is more rigid, and holds its shape better, than veins, which are relatively flimsy and which tend to flatten out when blood is withdrawn at a rate which exceeds the flow rate through the vein.

Thus it will be seen that the placement of suction line 225 in right atrium 70 permits blood to be withdrawn from the patient's vascular system at a greater rate during hemodialysis, without drawing the side walls of the surrounding vascular structure into mouth 245 of suction line 225. As a result, the throughput of the dialysis machine will be increased, whereby the dialysis time for each patient may be reduced and the number of patients serviced by each dialysis machine could be increased. This provides a significant advantage over the prior art.

It should also be appreciated that placement of suction line 225 in right atrium 70 will tend to reduce the risk of clot formation. This is because catheter contact with the side wall of the host blood vessel tends to promote clot formation. However, in the present case, mouth 245 of suction line 225 will tend to reside relatively far from the side walls of right atrium 70; hence, wall contact, and therefore clot formation, will tend to be reduced.

Figure 1:
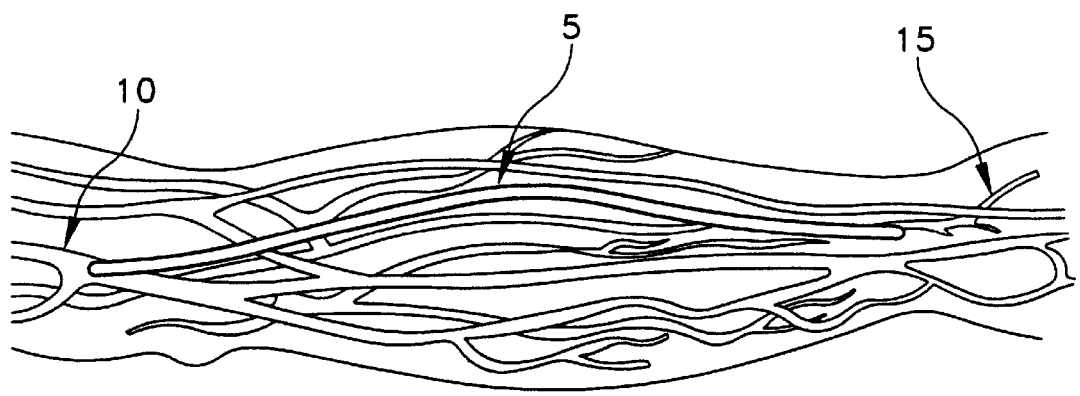
FIG. 1 is a schematic view of a PTFE graft in the arm of a patient.
Figure 2:
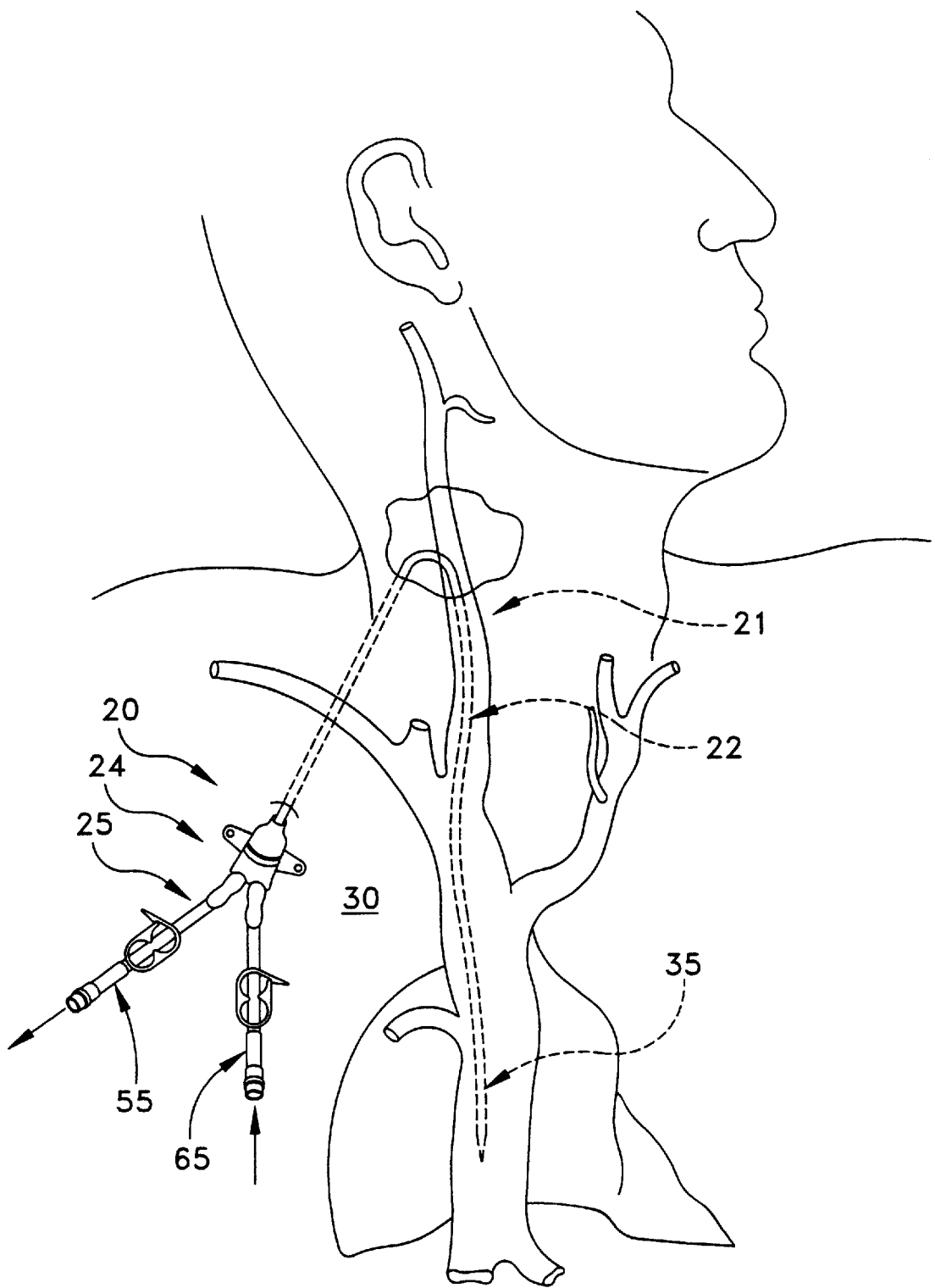
FIG. 2 is a schematic view of a prior art central venous percutaneous catheter assembly installed in a patient.

It should also be appreciated that it is possible to construct a new form of percutaneous catheter assembly which combines the prior art extracorporeal connector element 25 shown in FIG. 2 with the new catheter element 220 shown in FIG. 9, and to deploy it in the new manner shown in FIG. 9.

Figure 3:
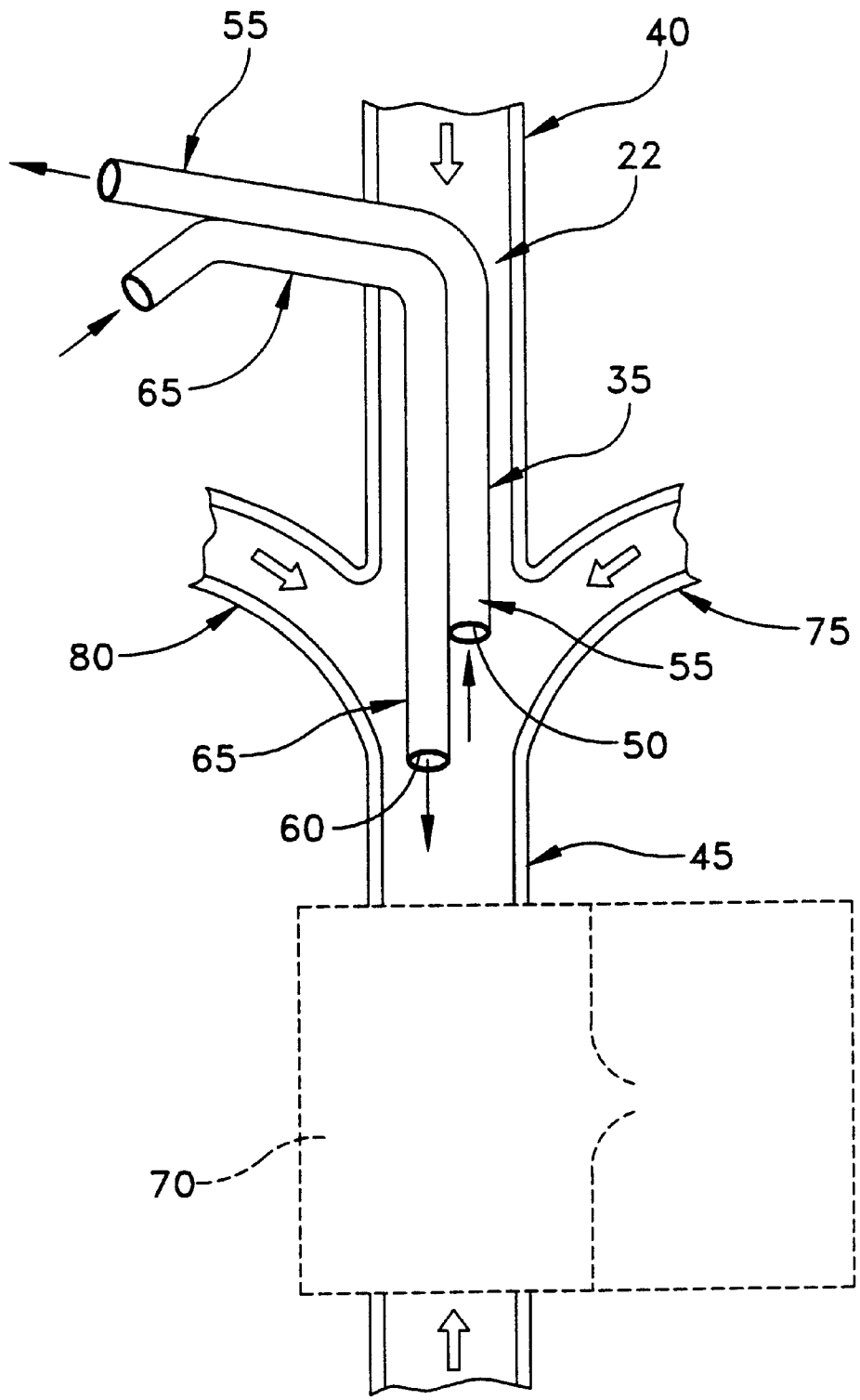
FIG. 3 is a schematic view showing the traditional method for installing the catheter element of the percutaneous catheter assembly of FIG. 2 in a human body, with the direction of blood flow being indicated by appropriate arrows.
Figure 4:
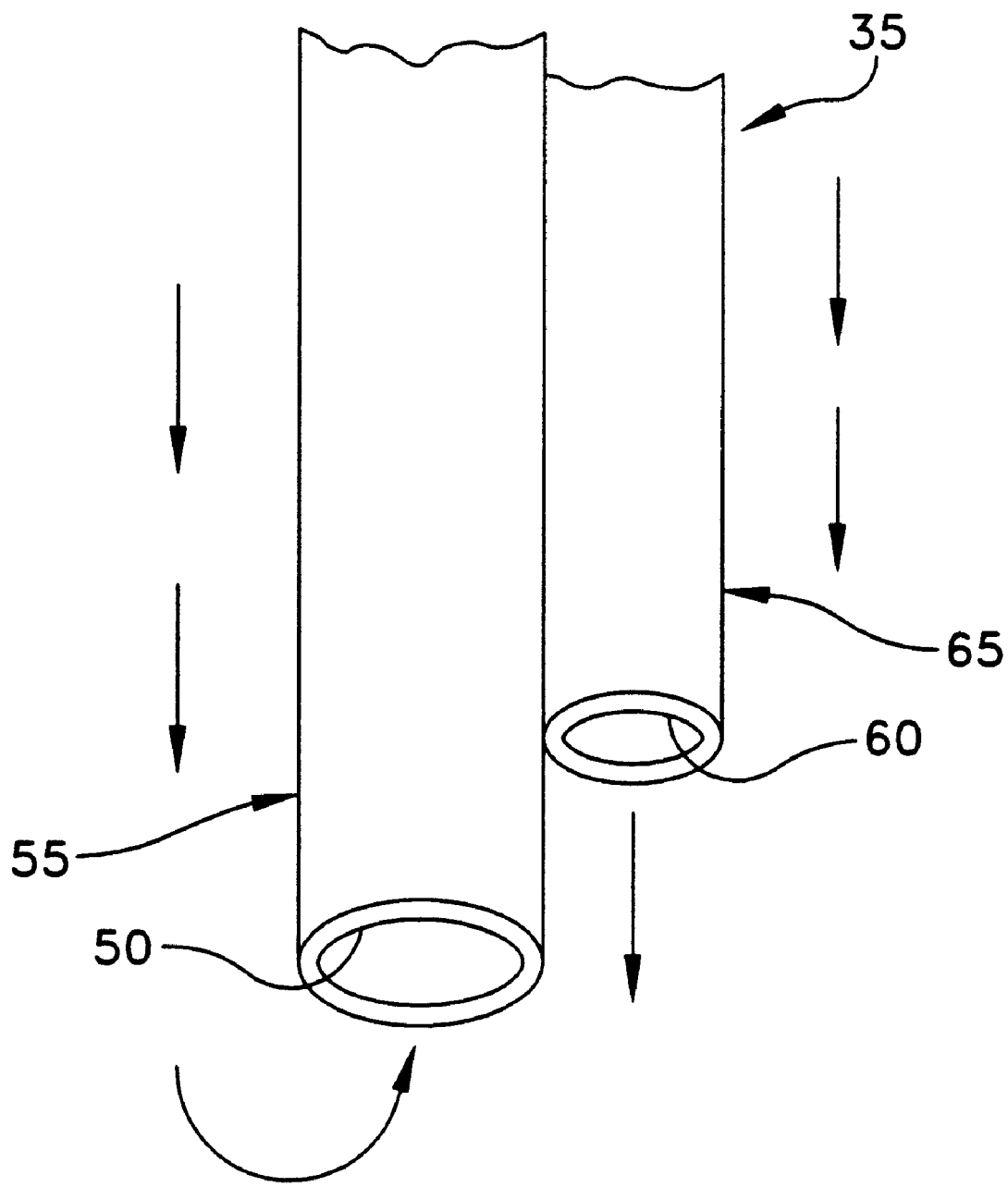
FIG. 4 shows an alternative construction for the distal end of the catheter element shown in FIG. 2.
Figure 6:
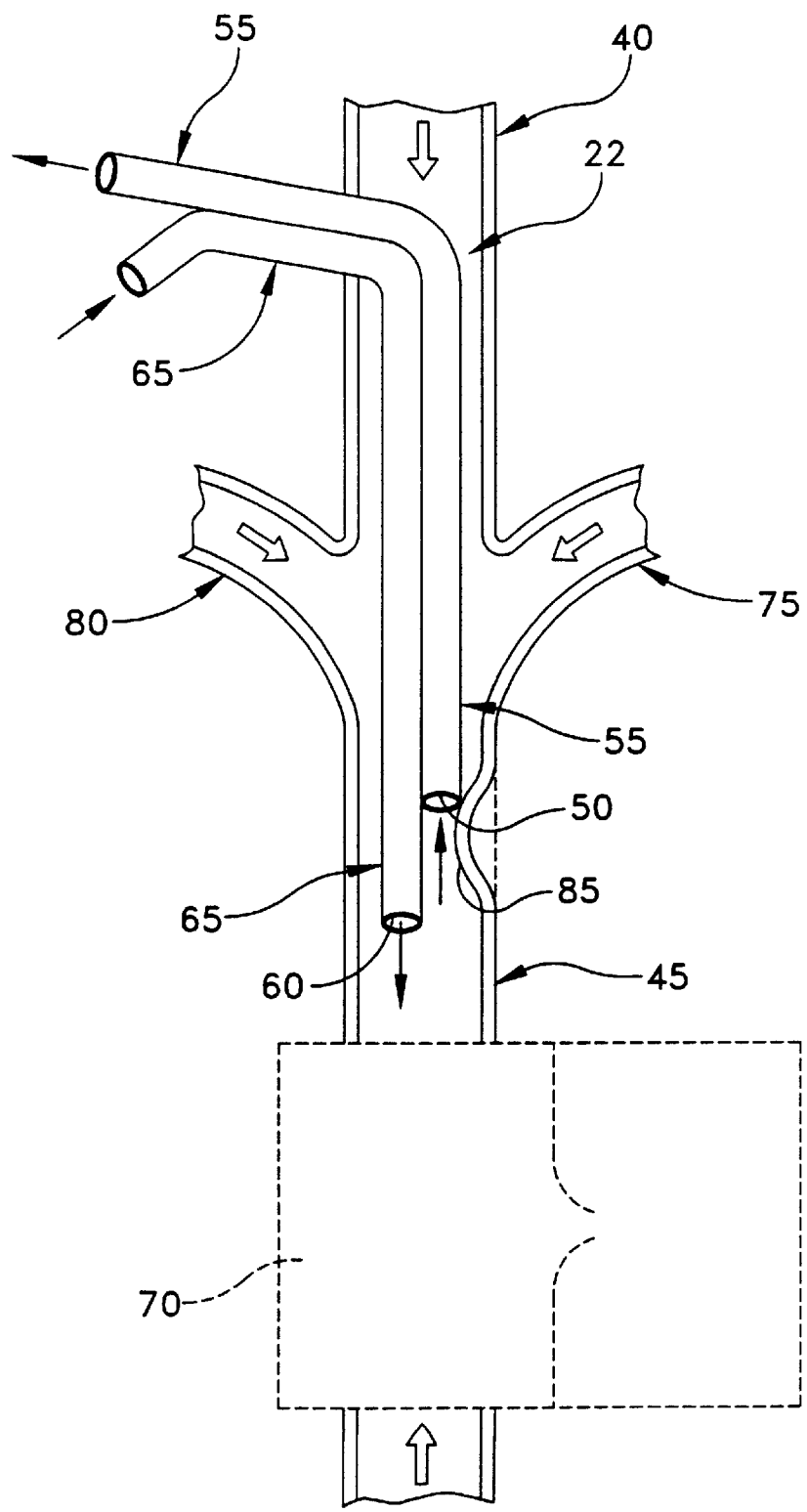
FIG. 6 is a schematic view showing how the traditional method for installing the percutaneous catheter assembly of FIGS. 2 and 3 in a human body may result in the side wall of the host blood vessel being drawn into the mouth of the percutaneous catheter assembly's suction line.
Figure 10:
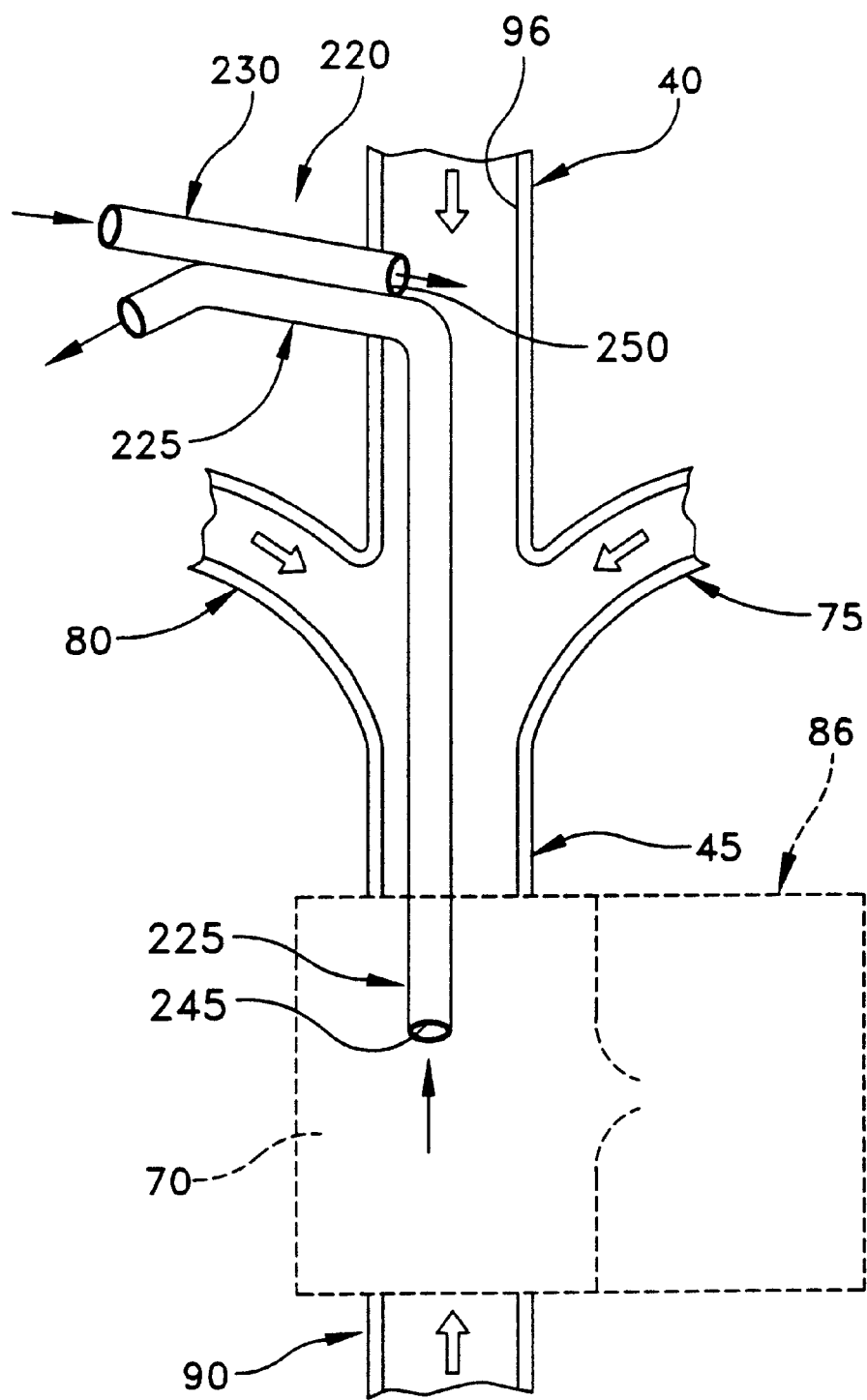
FIG. 10 is a schematic view showing an alternative method for installing the novel subcutaneous port and catheter assembly of FIG. 9 in a human body.

Looking next at FIG. 10, it will be seen that it is also possible to position mouth 250 of return line 230 just inboard of the side wall 96 of internal jugular vein 40. By utilizing such an arrangement, substantially only suction line 225 of assembly 205 needs to extend through the patient's internal jugular vein 40 and superior vena cava 45. As a result, suction line 225 can be formed with a diameter which is larger than (1) the diameter of suction line 55 of the prior art percutaneous catheter assembly 20 shown in FIGS. 2 and 3, and/or (2) the diameter of suction line 125 of catheter element 120 shown in FIG. 7, and/or (3) the diameter of suction line 225 of catheter element 220 shown in FIG. 9, without impeding the flow of blood through internal jugular vein 40 and superior vena cava 45. This permits blood to be withdrawn from, and restored to, the patient at increased flow rates, thereby increasing the throughput of the dialysis machine. Again, this could result in decreased dialysis time for each patient and thereby increase the number of patients who may be serviced by a given dialysis machine.

It should also be appreciated that it is possible to construct a new form of percutaneous catheter assembly which combines the prior art extracorporeal connector element 25 shown in FIG. 2 with the new catheter element 220 shown in FIG. 10, and to deploy it in the new manner shown in FIG. 10.

FIGS. 11–14 show still other alternative arrangements for positioning the distal end of assembly 205 within the patient's vascular system.

Figure 11:
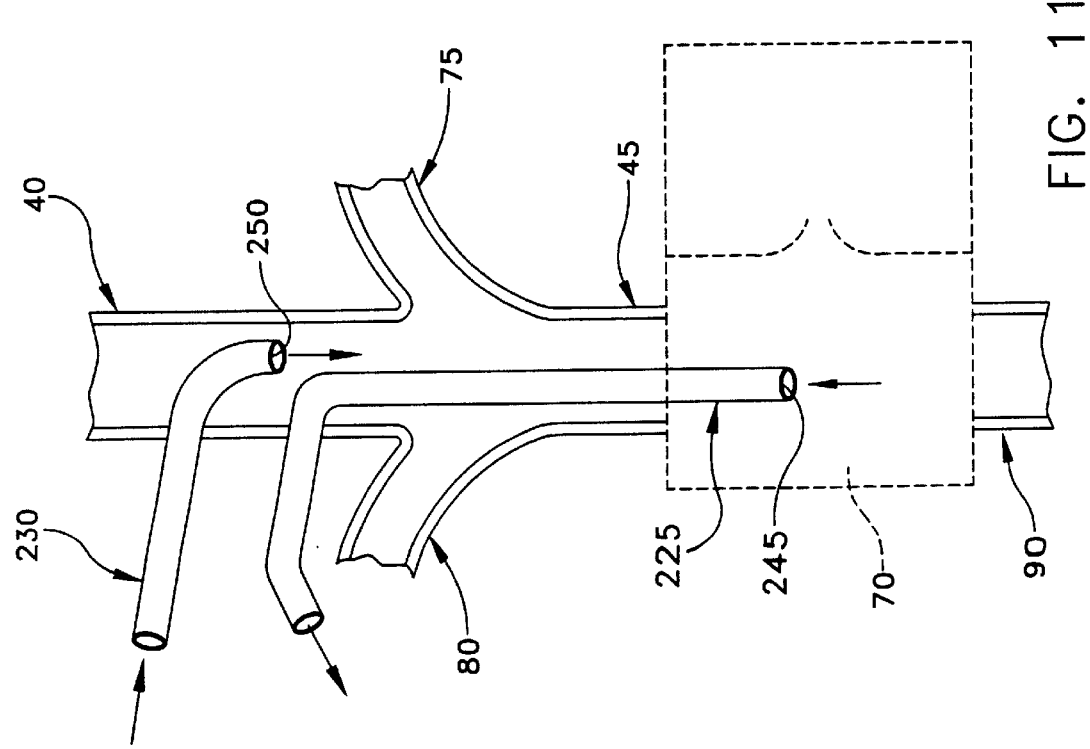

More particularly, FIG. 11 shows the distal end of return line 230 entering internal jugular vein 40 through one opening, and the distal end of suction line 225 entering superior vena cava 40 through another opening. Mouth 250 of return line 230 is disposed in internal jugular vein 40, while mouth 245 of suction line 225 is disposed in right atrium 70.

It should also be appreciated that it is possible to construct a new form of percutaneous catheter assembly which combines the prior art extracorporeal connector element 25 shown in FIG. 2 with the new catheter element 220 shown in FIG. 11, and to deploy it in the new manner shown in FIG. 11.

Figure 12:
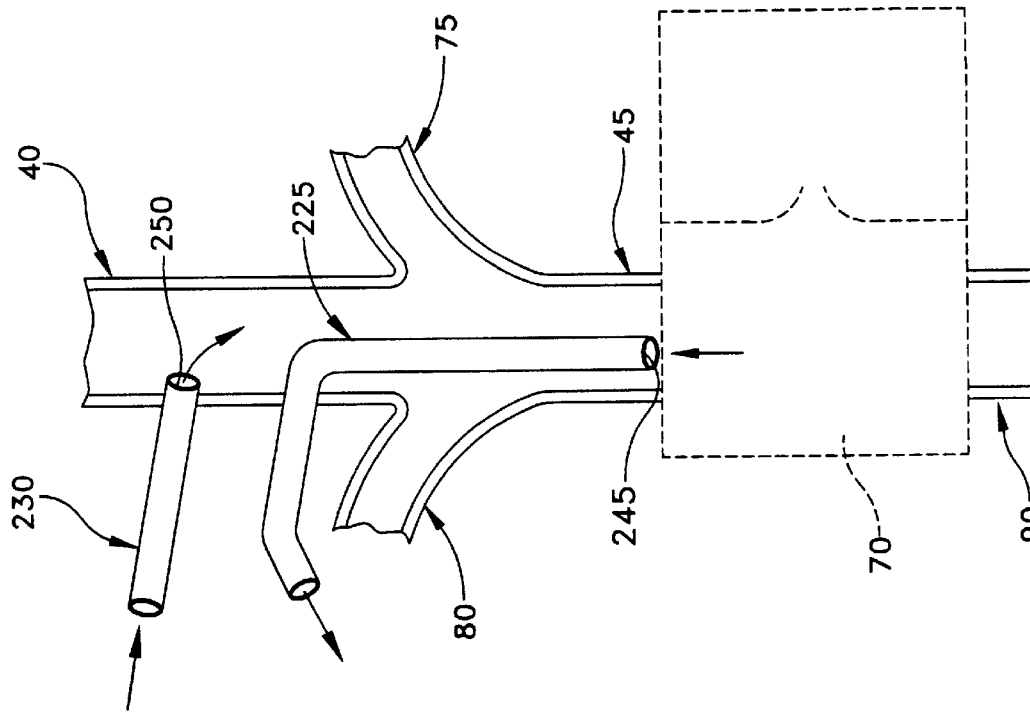

The arrangement shown in FIG. 12 is similar to the arrangement shown in FIG. 11, except that mouth 245 of suction line 225 is disposed in superior vena cava 45.

It should also be appreciated that it is possible to construct a new form of percutaneous catheter assembly which combines the prior art extracorporeal connector element 25 shown in FIG. 2 with the new catheter element 220 shown in FIG. 12, and to deploy it in the new manner shown in FIG. 12.

The arrangement shown in FIG. 13 is similar to the arrangement shown in FIG. 12, except that mouth 245 of suction line 225 is disposed in inferior vena cava 90.

It should also be appreciated that it is possible to construct a new form of percutaneous catheter assembly which combines the prior art extracorporeal connector element 25 shown in FIG. 2 with the new catheter element 220 shown in FIG. 13, and to deploy it in the new manner shown in FIG. 13.

The arrangement of FIG. 14 is similar to the arrangement of FIG. 13, except that the distal end of suction line 225 is passed directly into inferior vena cava 90 rather than into superior vena cava 40, down through right atrium 70 and then into inferior vena cava 90.

It should also be appreciated that it is possible to construct a new form of percutaneous catheter assembly which combines the prior art extracorporeal connector element 25 shown in FIG. 2 with the new catheter element 220 shown in FIG. 14, and to deploy it in the new manner shown in FIG. 14.

Figure 14A:
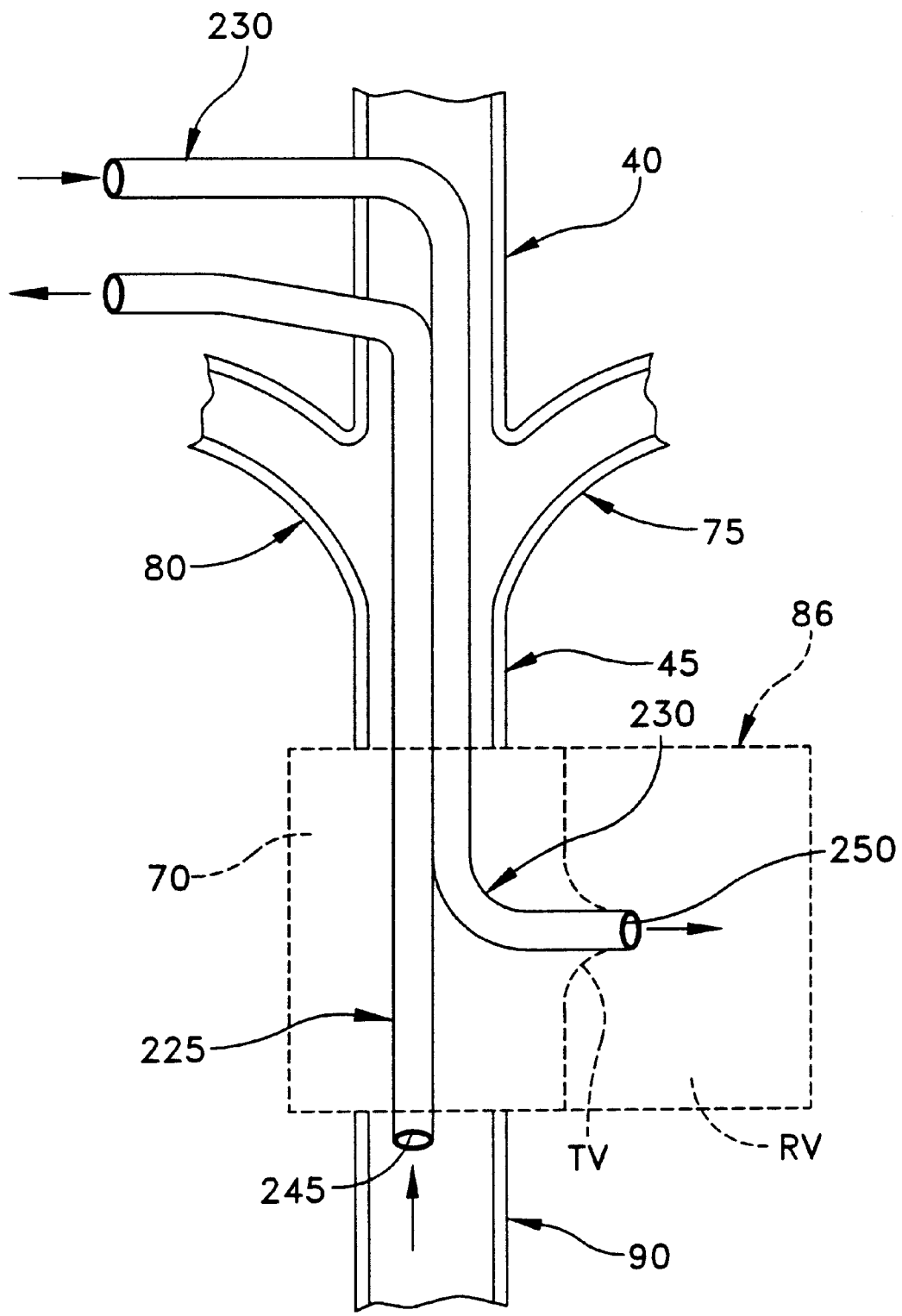

FIG. 14A shows still another possible arrangement for positioning the distal end of assembly 205 within the patient's vascular system. More particularly, mouth 245 of suction line 225 may be positioned in inferior vena cava 90, while mouth 250 of return line 230 is positioned within the right ventricle RV of heart 86, with the distal end of return line 230 extending through the heart's tri-cuspid valve TV. This arrangement results in negligible recirculation of the cleansed blood which is being returned to the patient by return line 230. As such, it will improve the efficiency of the dialysis process. Also, because this catheter placement is inherently free of recirculation, the relative positioning of mouth 245 of suction line 225 and mouth 250 of return line 230 is less critical than with other tip dispositions, and less precision is required in getting the right spacing between the mouths of the two lines.

If desired, mouth 245 of suction line 225 could be positioned within atrium 70 of heart 86, or within superior vena cava 45, while mouth 250 of return line 230 is positioned within right ventricle RV of heart 86.

If desired, a radio-opaque material can be applied to, or incorporated into, one or both of suction line 225 and return line 230, so that medical personnel can see the position of a line under fluoroscopy during catheter placement.

It should also be appreciated that it is possible to construct a new form of percutaneous catheter assembly which combines the prior art extracorporeal connector element 25 shown in FIG. 2 with the new catheter element 220 shown in FIG. 14A, and to deploy it in the new manner shown in FIG. 14A.

As noted above with respect to FIG. 10, mouth 250 of return line 230 may be positioned just inboard of side wall 96 of internal jugular vein 40 or the side wall 85 of superior vena cava 45. The constructions of FIGS. 15 and 16 expand upon this arrangement somewhat, by fastening return line 230 to the side wall 96 of internal jugular vein 40 or to the side wall 85 of superior vena cava 45.

Figure 15:
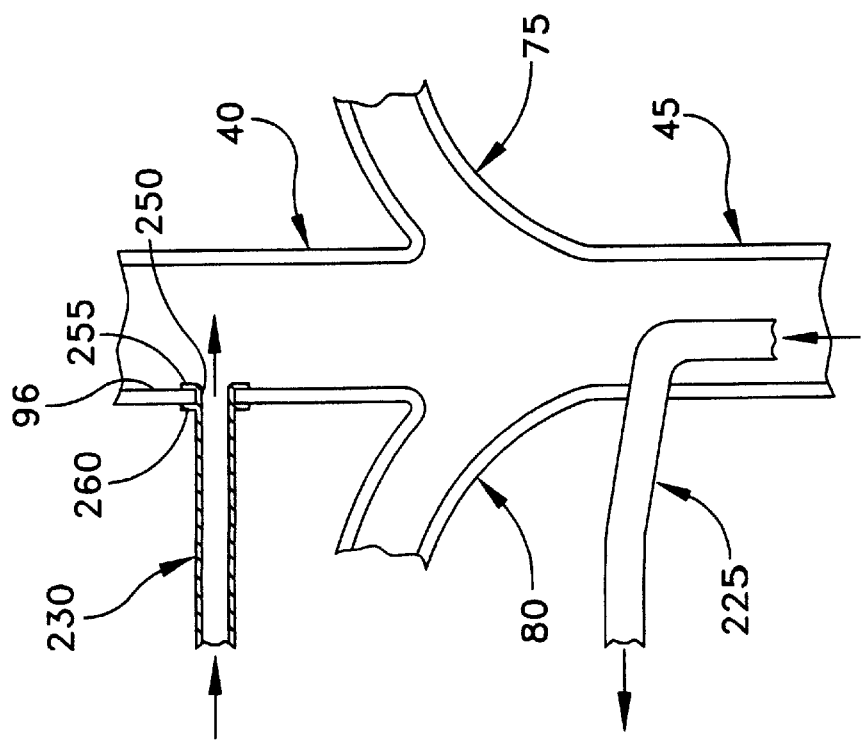
FIG. 15 is a schematic view showing another novel form of subcutaneous port and catheter assembly installed in a human body.

More particularly, and looking now at FIG. 15, return line 230 may be connected to the patient's vascular system using its own opening, and it may be held fast to the patient's vascular tissue by means of a flange 255 and a corresponding locking collar 260. Preferably flange 255 is formed without any sharp edges which might impede blood flow or induce blood clotting. In use, mouth 250 of return line 230 is passed into the interior of internal jugular vein 40 (or superior vena cava 45) so that flange 255 sits against the inner wall of the blood vessel, and then locking collar 260 is slid distally down return line 230 so as to capture the wall of the blood vessel between flange 255 and locking collar 260.

It should also be appreciated that it is possible to construct a new form of percutaneous catheter assembly which combines the prior art extracorporeal connector element 25 shown in FIG. 2 with the new catheter element 220 shown in FIG. 15, and to deploy it in the new manner shown in FIG. 15.

Figure 16:
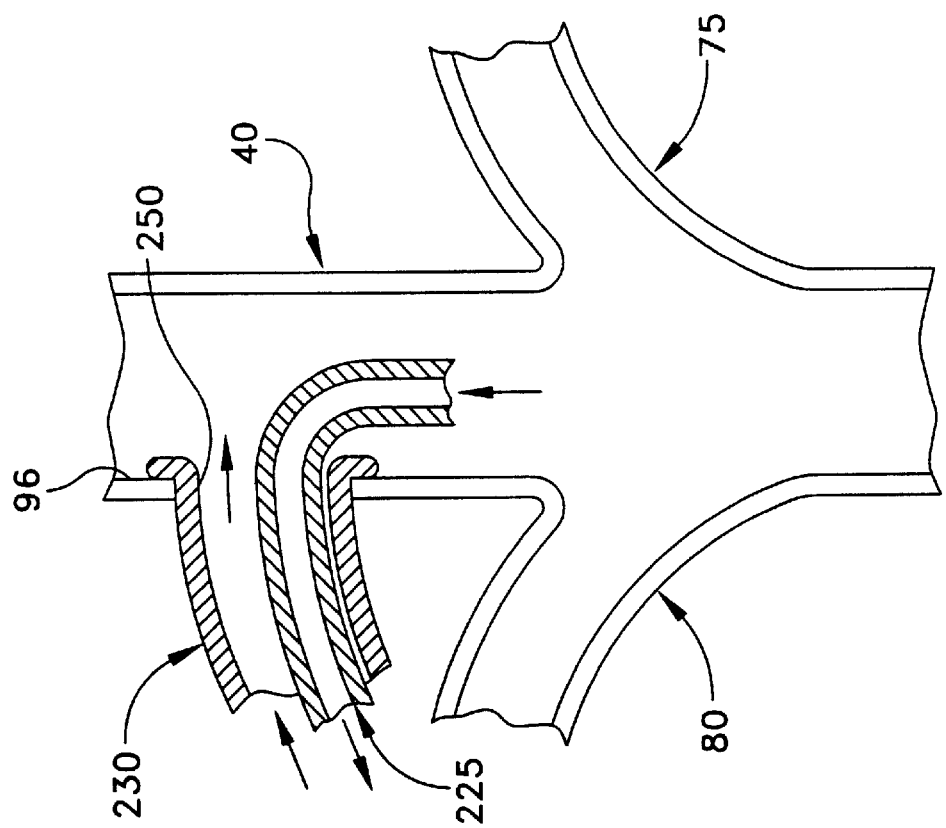
FIG. 16 is a schematic view showing another novel form of subcutaneous port and catheter assembly installed in a human body.

FIG. 16 is similar to FIG. 15, except that return line 230 is formed with an enlarged diameter and suction line 225 is passed through the interior of return line 230 so as to communicate with the patient's vascular system. It will be appreciated that, with the construction shown in FIG. 16, mouth 245 (not shown) of suction line 225 is advanced a substantial distance beyond mouth 250 of return line 230 in order to avoid the blood recirculation problems mentioned above.

It should also be appreciated that it is possible to construct a new form of percutaneous catheter assembly which combines the prior art extracorporeal connector element 25 shown in FIG. 2 with the new catheter element 220 shown in FIG. 16, and to deploy it in the new manner shown in FIG. 16.

It is also possible to modify the configuration of assembly 205 so as to minimize the possibility of mouth 245 of suction line 225 contacting the side wall of its host blood vessel, and/or to minimize the possibility of tissue growing around the distal end of suction line 225 and occluding mouth 245 of suction line 225. Such tissue growth can occur during the quiescent periods between active dialysis sessions.

Figure 17:
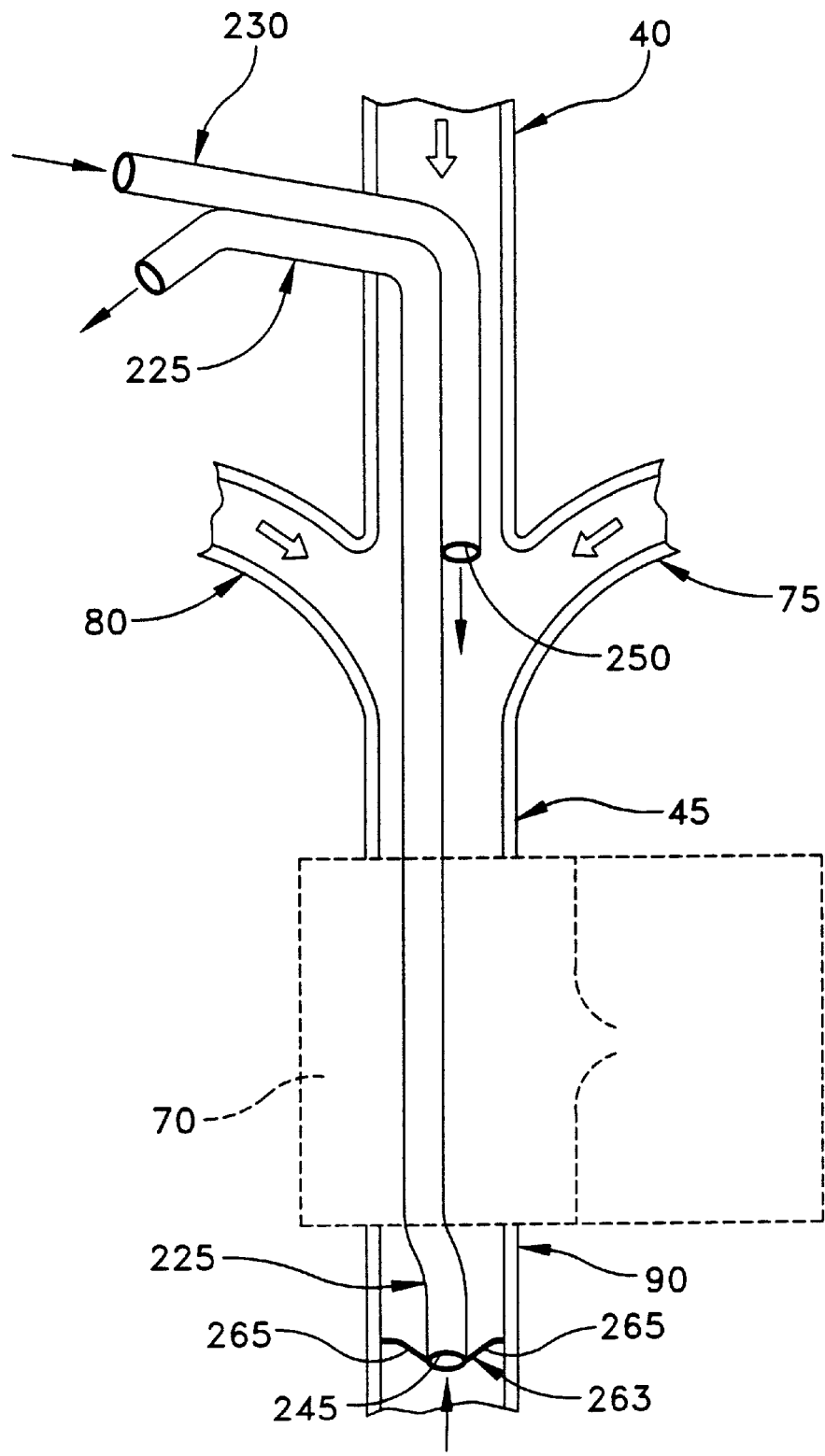
FIG. 17 is a schematic view showing still another novel form of subcutaneous port and catheter assembly installed in a human body.

For example, and looking next at FIG. 17, mouth 245 of suction line 225 is shown disposed in the patient's inferior vena cava 90. In order to center mouth 245 within inferior vena cava 90, the distal end of suction line 225 includes a multi-legged support 263. The legs 265 of support 263 extend between the distal end of suction line 225 and the surrounding wall of the host blood vessel so as to stabilize suction line 225 within the blood vessel and keep its mouth 245 centered. At the same time, blood can pass unrestricted between the legs of support 263.

It should also be appreciated that it is possible to construct a new form of percutaneous catheter assembly which combines the prior art extracorporeal connector element 25 shown in FIG. 2 with the new catheter element 220 shown in FIG. 17, and to deploy it in the new manner shown in FIG. 17.

If desired, support 263 can also be used to center the distal end of suction line 225 in the patient's superior vena cava 45 rather than in the patient's inferior vena cava 90.

Alternatively, where the distal end of return line 230 may be free to move about within its host blood vessel (see, for example, the arrangement shown in FIG. 11), the distal end of return line 230 might be fitted with its own support 263.

Figure 18:
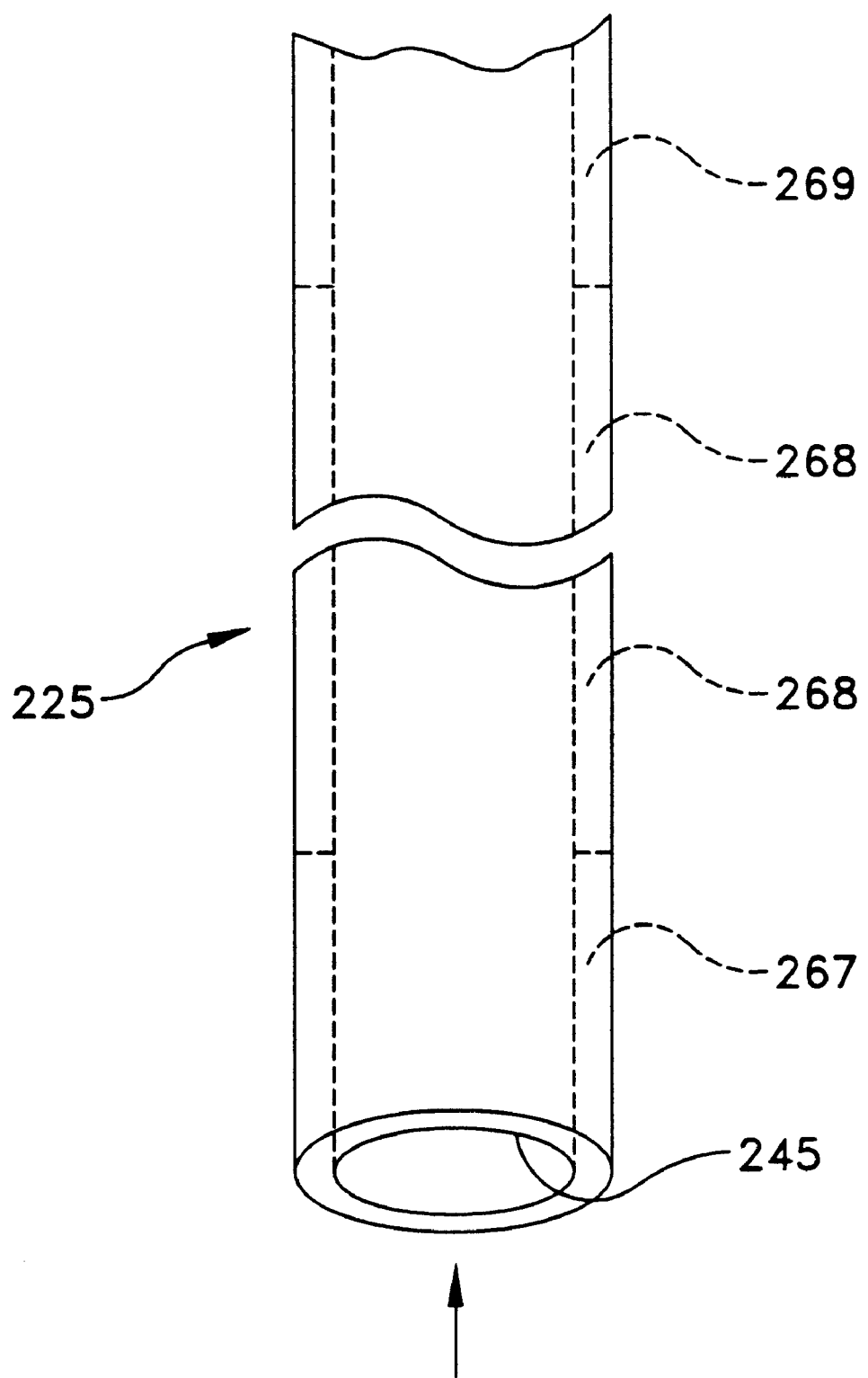
FIG. 18 is a schematic view of the distal end of another novel form of subcutaneous port and catheter assembly formed in accordance with the present invention.

FIG. 18 shows still another possible construction for the distal end of suction line 225. Here, the suction line might comprise a relatively soft material 267 adjacent to mouth 245, a relatively stiff material 268 just proximal thereto, and a relatively flexible material 269 for the main body of suction line 225. With this construction, the relatively stiff material 268 can help keep suction line 225 centered in its host blood vessel, while the relatively soft material 267 can help cushion any contact which might occur between the suction line and a vascular structure during deployment and/or use of the suction line. In particular, the relatively stiff material 268 can help keep suction line 225 from unintentionally straying into the heart's tri-cuspid valve TV (FIG. 14A) when mouth 245 of suction line 225 is within right atrium 70, and it can help pass mouth 245 of suction line 225 into inferior vena cava 90 if mouth 245 is to be disposed in such a position. Furthermore, the presence of relatively stiff material 268 in the distal tip of suction line 225 can help keep the tip of the suction line from doubling back on itself, in a sort of U-shaped manner, which can sometimes happen with soft catheter lines.

It should also be appreciated that it is possible to construct a new form of percutaneous catheter assembly which combines the prior art extracorporeal connector element 25 shown in FIG. 2 with the new catheter element 220 shown in FIG. 18.

Again, where the distal end of return line 230 may be free to move about within its host blood vessel (see, for example, the arrangement shown in FIG. 11), the distal end of return line 230 might be formed in a manner corresponding to that shown in FIG. 18.

It is also possible to form suction line 125 and/or return line 130 of catheter element 120 (FIG. 8) in the manner shown in FIG. 18.

Figure 19:
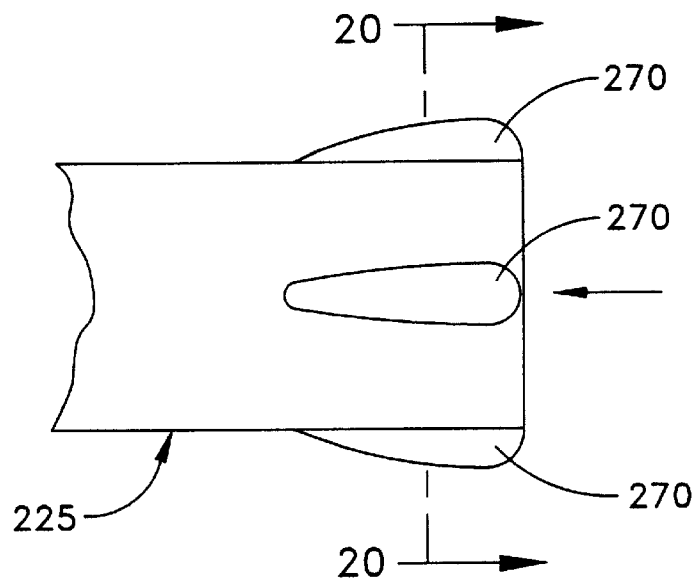
FIG. 19 is a schematic view showing the distal end of yet another novel form of subcutaneous port and catheter assembly formed in accordance with the present invention.
Figure 20:
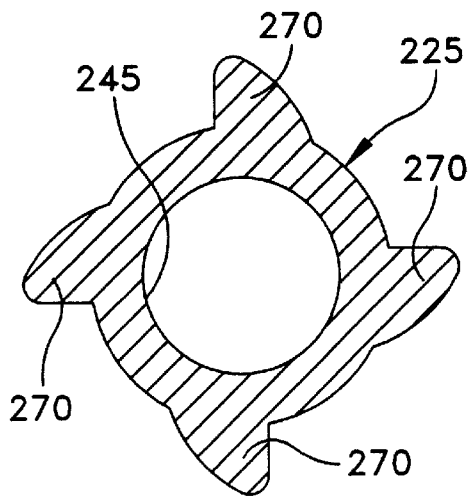
FIG. 20 is a sectional view taken along line 20—20 of FIG. 19.

Looking next at FIGS. 19 and 20, there is shown still another alternative construction for the distal tip of suction line 225. The distal tip includes spacer fins or bumpers 270 which keep mouth 245 of suction line 225 spaced some distance away from the side wall of its host blood vessel. This construction will help minimize the possibility of mouth 245 contacting the side wall of its host blood vessel, and/or the possibility of tissue growing out of the side wall of the host blood vessel and encapsulating, or otherwise occluding, mouth 245 of suction line 225.

It should also be appreciated that it is possible to construct a new form of percutaneous catheter assembly which combines the prior art extracorporeal connector element 25 shown in FIG. 2 with the new catheter element 220 shown in FIGS. 19 and 20.

Again, where the distal end of return line 230 may be free to move about within its host blood vessel (see, for example, the arrangement shown in FIG. 11), the distal end of return line 230 might be fitted with its own spacer fins 270.

It is also possible to form suction line 125 and/or return line 130 of catheter element 120 (FIG. 8) in the manner shown in FIGS. 19 and 20.

Figure 21:
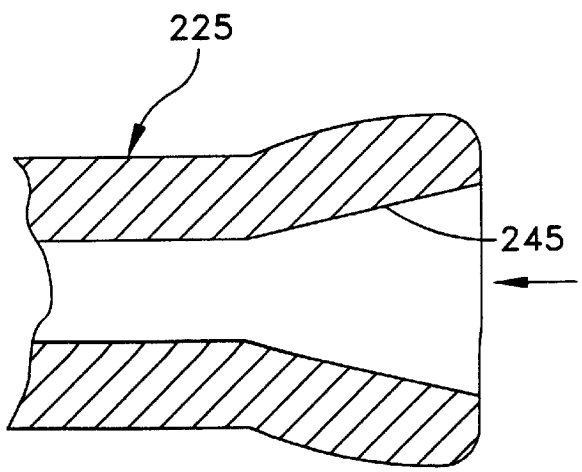
FIG. 21 is a schematic view showing the distal end of still another novel form of subcutaneous port and catheter assembly formed in accordance with the present invention.

Looking next at FIG. 21, there is shown still another possible construction for the distal tip of suction line 225. With this construction, the mouth 245 of suction line 225 is configured with a gradual inward taper so as to provide a streamlined flow path for the blood entering suction line 225. Such a streamlined flow path enhances entry of the patient's blood into suction line 225 by reducing entrance pressure losses and helps avoid blood clotting.

It should also be appreciated that it is possible to construct a new form of percutaneous catheter assembly which combines the prior art extracorporeal connector element 25 shown in FIG. 2 with the new catheter element 220 shown in FIG. 21.

If desired, a similar configuration can be provided for mouth 250 of return line 230.

And it is possible to form suction line 125 and/or return line 130 of catheter element 120 (FIG. 8) in the manner shown in FIG. 21.

Figure 22:
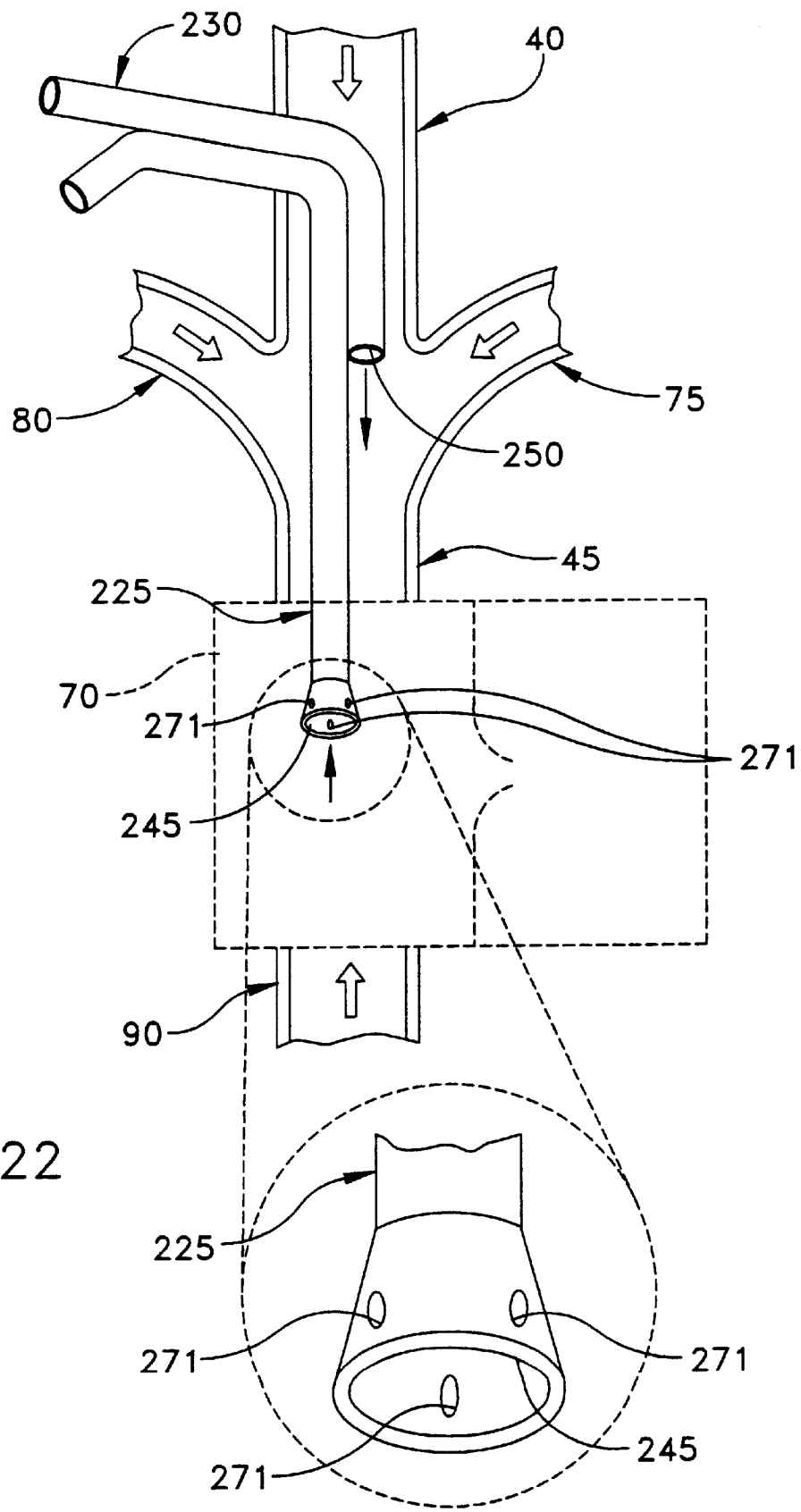
FIG. 22 is a schematic view showing the distal end of yet another novel form of subcutaneous port and catheter assembly formed in accordance with the present invention.

FIG. 22 illustrates still another possible construction for minimizing the possibility of tissue or other debris occluding the mouth of suction line 225. More particularly, the distal end of suction line 225 is preferably formed with a bell-shaped configuration and includes an inwardly-tapered mouth 245 along the lines of that shown in FIG. 21. In addition, however, the distal end of suction line 225 also includes a plurality of side openings 271 which extend through the side wall of suction line 225. Side openings 271 permit fluid to enter suction line 225 even if the mouth 245 of the suction line should be occluded with debris.

It should also be appreciated that it is possible to construct a new form of percutaneous catheter assembly which combines the prior art extracorporeal connector element 25 shown in FIG. 2 with the new catheter element 220 shown in FIG. 22.

It is also possible to form suction line 125 of catheter element 120 (FIG. 8) in the manner shown in FIG. 22.

Figure 24:
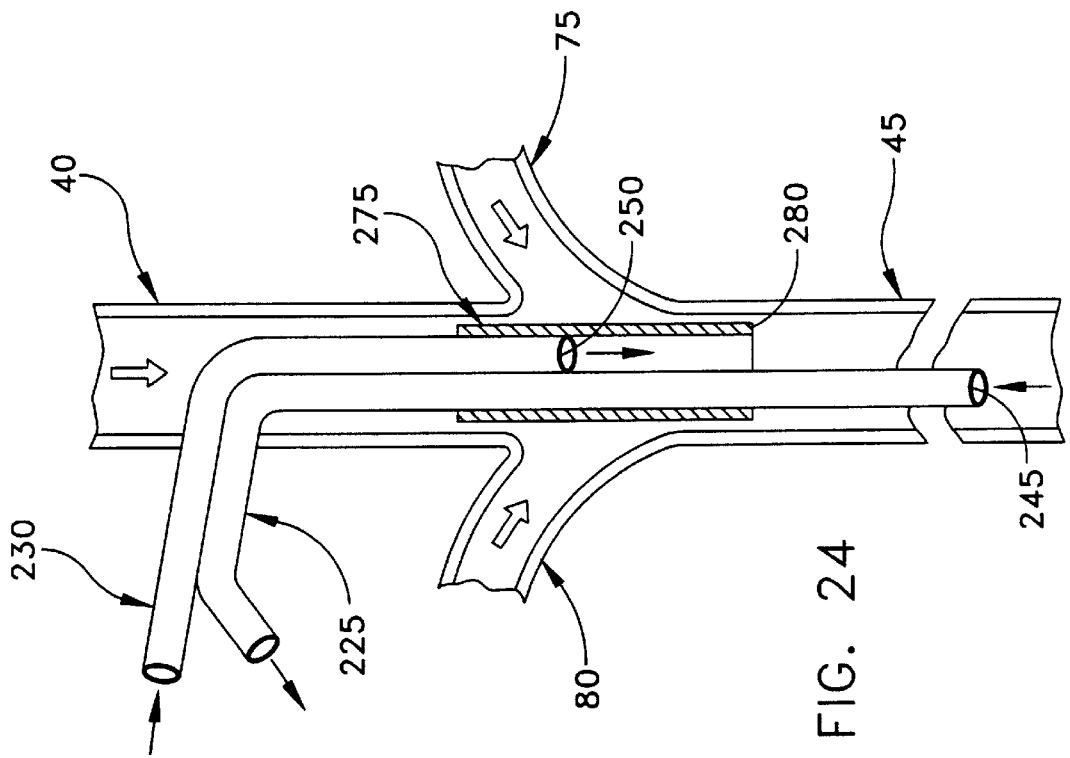
FIG. 24 is a schematic view like that of FIG. 23, but with the assembly being shown during the dialysis system's active state.
Figure 23:
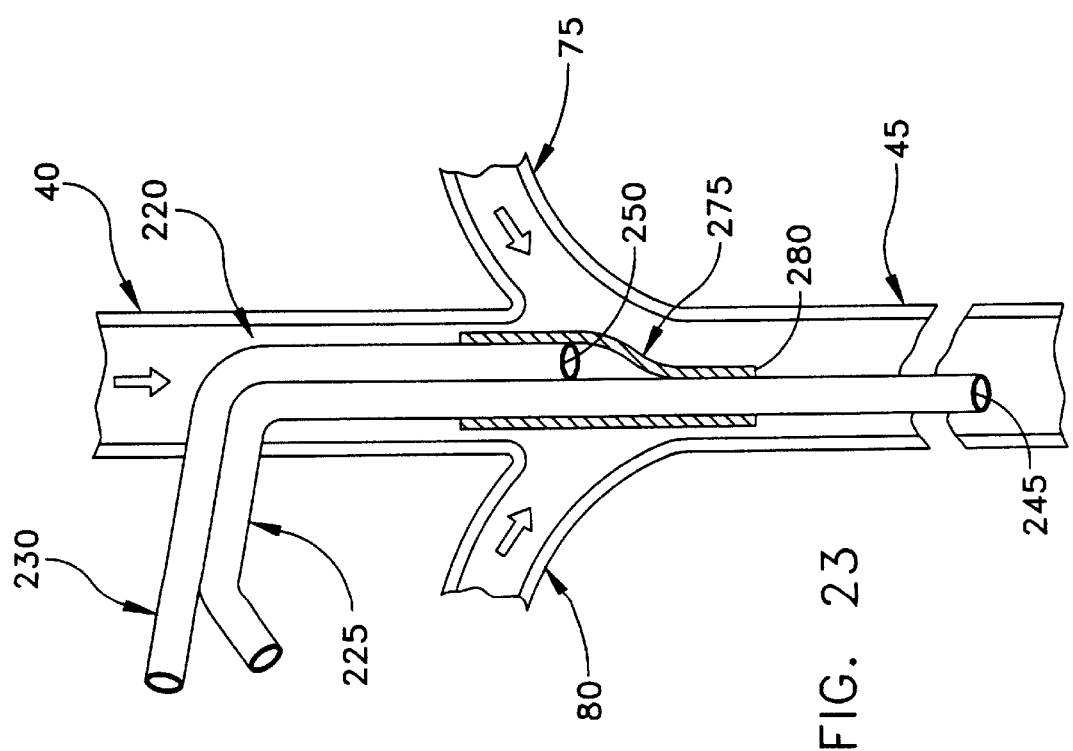
FIG. 23 is a schematic view showing the distal end of still another novel form of subcutaneous port and catheter assembly, with the assembly being shown during the dialysis system's quiescent state.

FIGS. 23 and 24 illustrate a construction for minimizing the possibility of tissue or other debris occluding the mouth of return line 230. More particularly, a resilient sleeve 275 may be positioned about part of the exterior of catheter element 220, such that the sleeve's distal end 280 extends beyond mouth 250 of return line 230, but terminates on the proximal side of mouth 245 of suction line 225. The elastic nature of sleeve 275 will cause it to contract down about suction line 225 and return line 230 during the system's quiescent state (FIG. 23), thereby protectively covering mouth 250 of return line 230. At the same time, however, the elastic nature of sleeve 275 will permit the sleeve to open so as to allow blood to flow out of mouth 250 of return line 230 during an active dialysis session (FIG. 24). Thus, with this construction, sleeve 275 protects mouth 250 of return line 230 from occlusion during the system's lengthy quiescent periods (FIG. 23), but will permit return line 230 to pass blood back to the body during a subsequent active dialysis session (FIG. 24).

It should also be appreciated that it is possible to construct a new form of percutaneous catheter assembly which combines the prior art extracorporeal connector element 25 shown in FIG. 2 with the new catheter element 220 shown in FIGS. 23 and 24.

Figure 25:
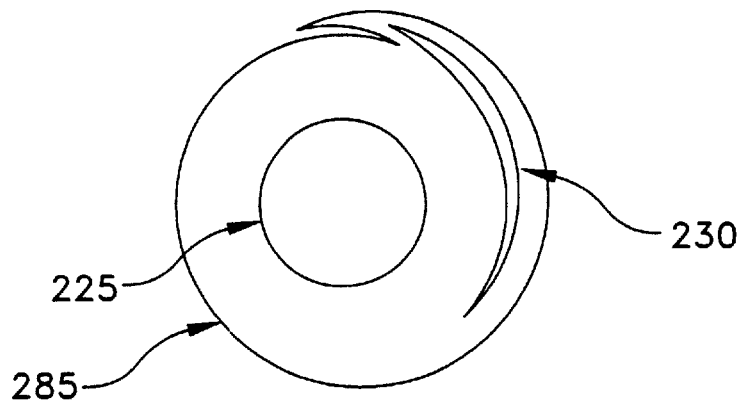
FIG. 25 is a schematic view of the distal end of still another novel form of subcutaneous port and catheter assembly formed in accordance with the present invention, with the assembly being shown during the dialysis system's quiescent state.
Figure 26:
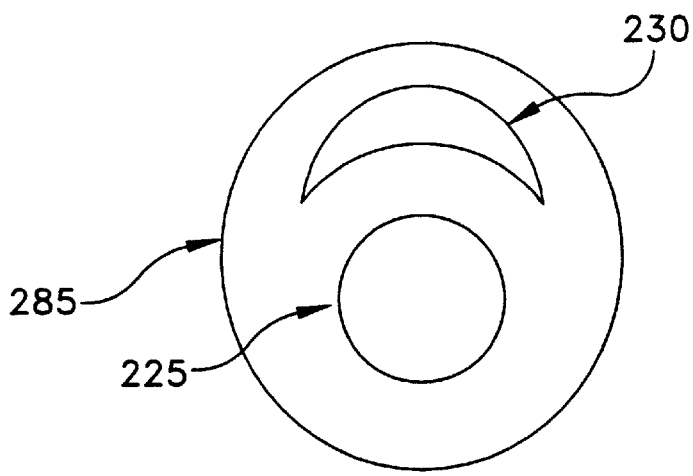
FIG. 26 is a schematic view like that of FIG. 25, but with the assembly being shown during the dialysis system's active state.

Looking next at FIGS. 25 and 26, there is shown an alternative construction for the distal end of assembly 205. With this alternative construction, suction line 225 and return line 230 are incorporated within a single tube 285. Furthermore, tube 285 is fabricated at least in part out of an elastomeric material, such that (i) during the system's quiescent state (FIG. 25), return line 230 will be in a reduced size condition due to the lack of blood flow therethrough, and (ii) during the system's active dialysis state (FIG. 26), return line 230 will be inflated in size due to the passage of blood therethrough. As a result of this construction, the assembly's return line 230 will occupy a reduced volumetric area within its host blood vessel during the system's quiescent state.

It is also possible to form catheter element 120 (FIG. 8) in the manner shown in FIGS. 25 and 26.

Figure 27:
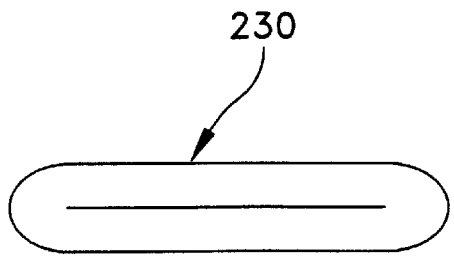
FIG. 27 is a schematic view of a portion of the distal end of yet another novel form of subcutaneous port and catheter assembly formed in accordance with the present invention, with the assembly being shown during the dialysis system's quiescent state.
Figure 28:
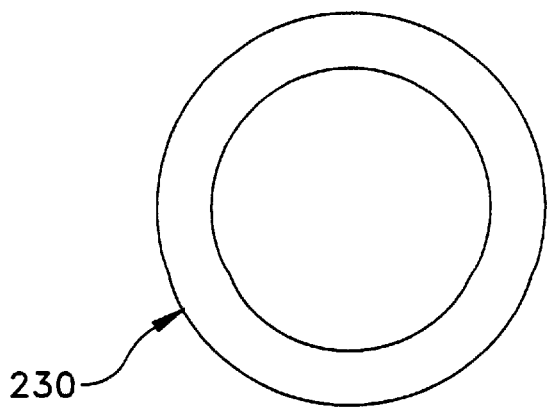
FIG. 28 is a schematic view like that of FIG. 27, but with the assembly being shown during the dialysis system's active state.

FIGS. 27 and 28 show another alternative construction for the assembly's return line 230. With this construction, the return line 230 is formed out of an elastomeric material, such that the return line will be in a reduced size condition during the system's quiescent state (FIG. 27), yet can become enlarged in size due to the passage of blood therethrough during the system's active dialysis state (FIG. 28).

It is also possible to form return line 130 of catheter element 120 (FIG. 8) in the manner shown in FIGS. 27 and 28.

Figure 29:
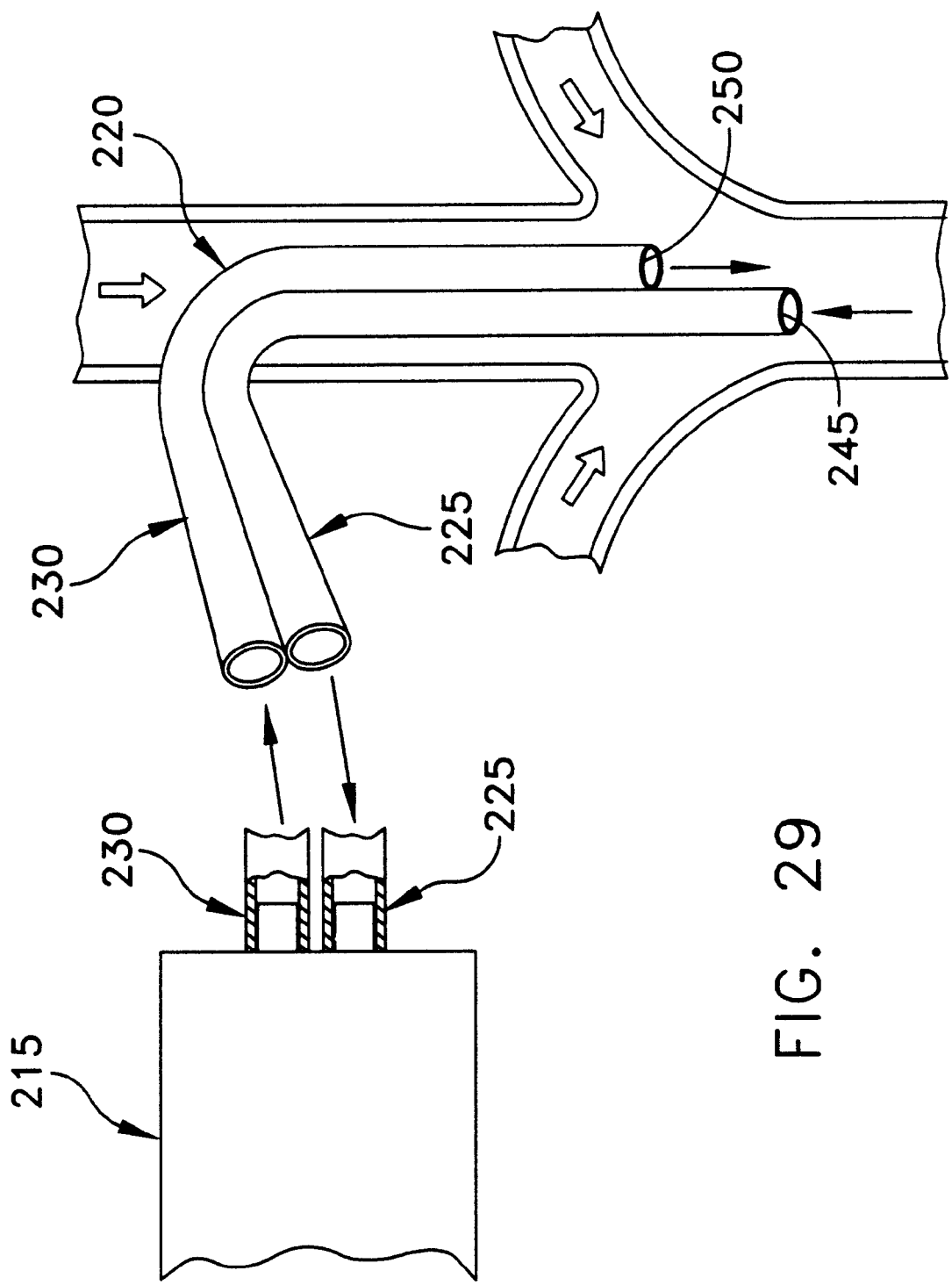
FIG. 29 is a schematic view of still another novel form of subcutaneous port and catheter assembly formed in accordance with the present invention.

Looking next at FIG. 29, there is shown still another embodiment of the present invention. More particularly, with this construction, suction line 225 and return line 230 are formed so that they have a larger internal diameter at their proximal ends than at their distal ends, with the two lines gradually tapering inward along their length. Such a construction is advantageous inasmuch as it can significantly reduce flow resistance to the blood moving through these lines.

It should also be appreciated that it is possible to construct a new form of percutaneous catheter assembly which combines the prior art extracorporeal connector element 25 shown in FIG. 2 with the new catheter element 220 shown in FIG. 29.

It is also possible to form suction line 125 and return line 130 of catheter element 120 (FIG. 8) in the manner shown in FIG. 29.

In some situations, it has been found that the catheter element can kink at the point where it bends to enter internal jugular vein 40, due to the large deflection required of the catheter element at this location. In many cases the thickness of the walls of the catheter element must be increased to avoid such kinking.

Figure 30:
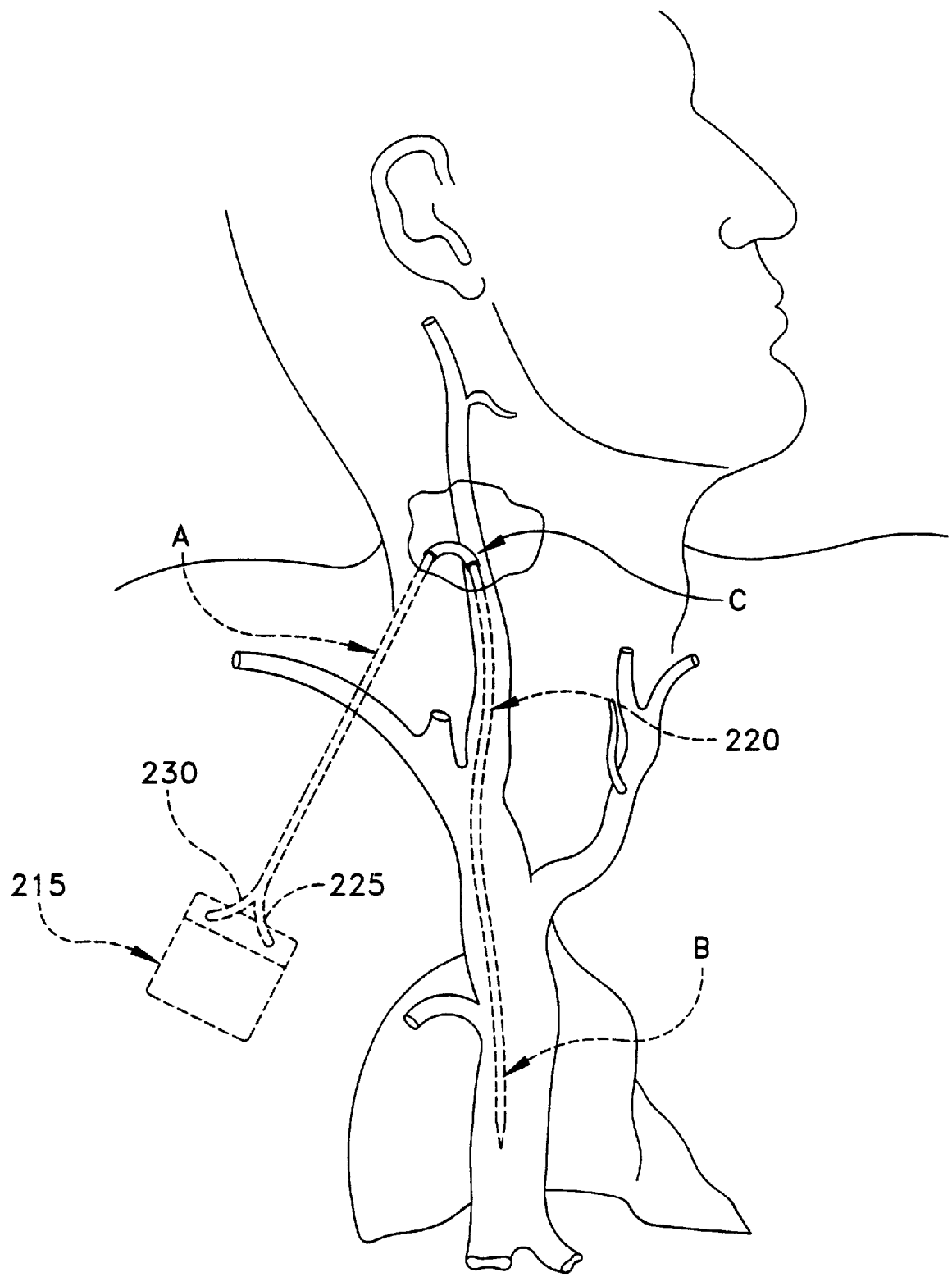
FIG. 30 is a schematic view of yet another novel form of subcutaneous port and catheter assembly formed in accordance with the present invention.

Looking next at FIG. 30, there is shown an embodiment of the present invention which is intended to remedy this problem. Here, catheter element 220 (comprising suction line 225 and return line 230) is formed in two dual-lumen halves, a proximal half A and a distal half B. The proximal half A and the distal half B are connected together by a generally curved dual-lumen coupling element C so as to form the complete catheter element 220. Curved coupling element C is preferably formed out of a fairly rigid material. The proximal end of proximal half A is connected to subcutaneous port element 215. The generally curved coupling element C is intended to be positioned at the point where catheter element 220 enters the patient's internal jugular vein 40, and it is curved so that the catheter element's proximal half A and its distal half B can both extend relatively straight through the body. If desired, the interior diameter of curved coupling element C can be tapered, as can the internal diameter of one or both of proximal half A and distal half B, in a manner similar to that shown in FIG. 29.

In use, the length of distal half B is first determined; then distal half B is trimmed at its proximal end to achieve this length. Next, the proximal end of distal half B is attached to coupling element C. Then the distal end of proximal half A is connected to coupling element C. Next, the proximal end of proximal half A is tunneled under the patient's skin, to the area where subcutaneous port element 215 will be deployed. Then a pocket is made for subcutaneous port element 215, the port element is placed in the pocket, and then the proximal end of proximal half A is trimmed to length and attached to port element 215.

By making coupling element C with a curved configuration, both halves of catheter element 220 (i.e., proximal half A and distal half B) can extend relatively straight through the body. Furthermore, by making coupling element C out of a fairly rigid material, kinking can be avoided even where the side walls of connector C are formed so as to be fairly thin.

Figure 31:
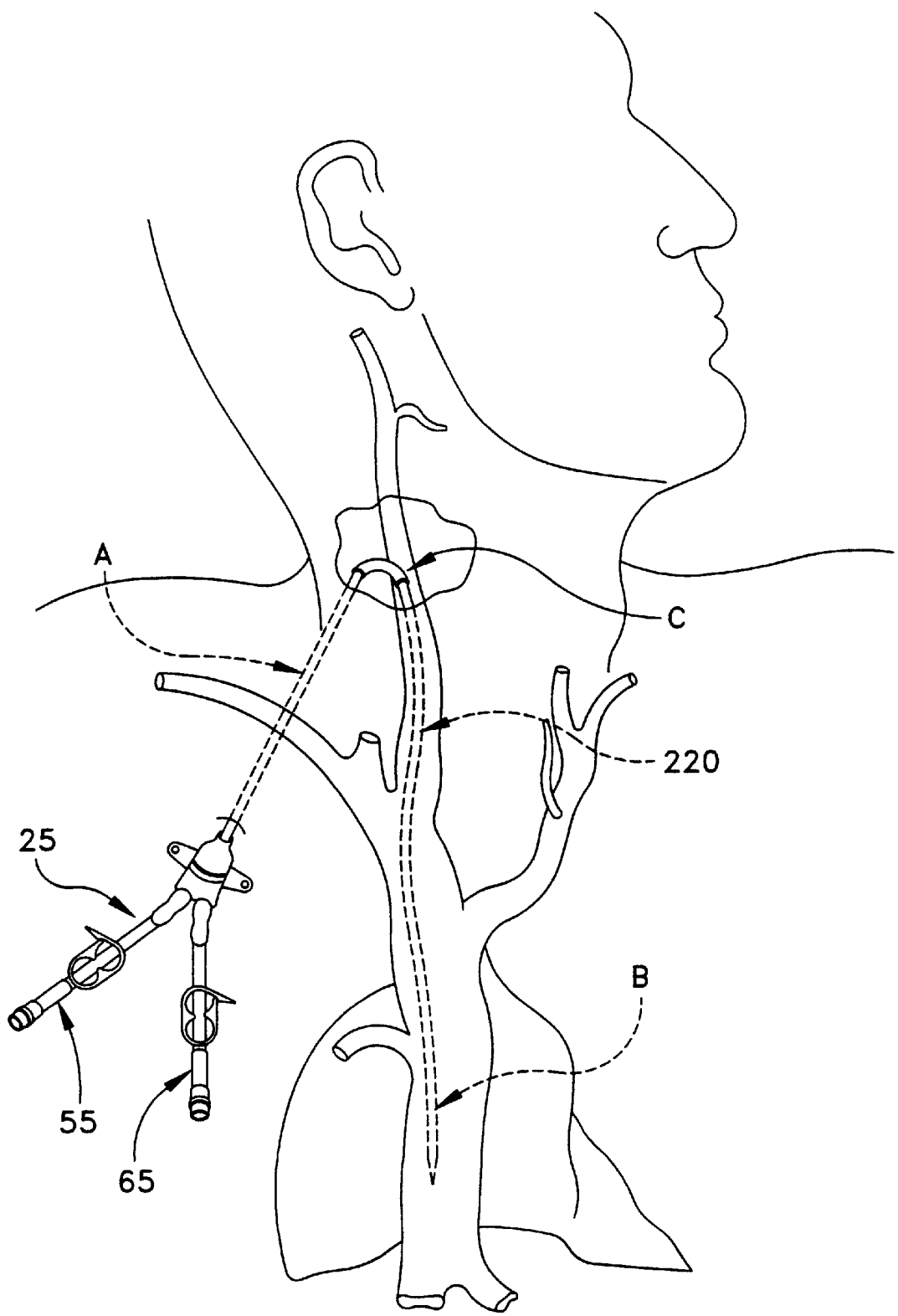
FIG. 31 is a schematic view of a novel central venous percutaneous catheter assembly formed in accordance with the present invention.

It should also be appreciated that it is possible to construct a new form of percutaneous catheter assembly which combines the prior art extracorporeal connector element 25 shown in FIG. 2 with the new catheter element 220 shown in FIG. 30, and to deploy it in the new manner shown in FIG. 30. See, for example, FIG. 31.

It is also possible to form catheter element 120 (FIG. 8) in the manner shown in FIG. 30.

As noted above, in some situations it has been found that the catheter element can kink at the point where it bends to enter internal jugular vein 40, due to the large deflection required of the catheter element at this location.

Figure 32:
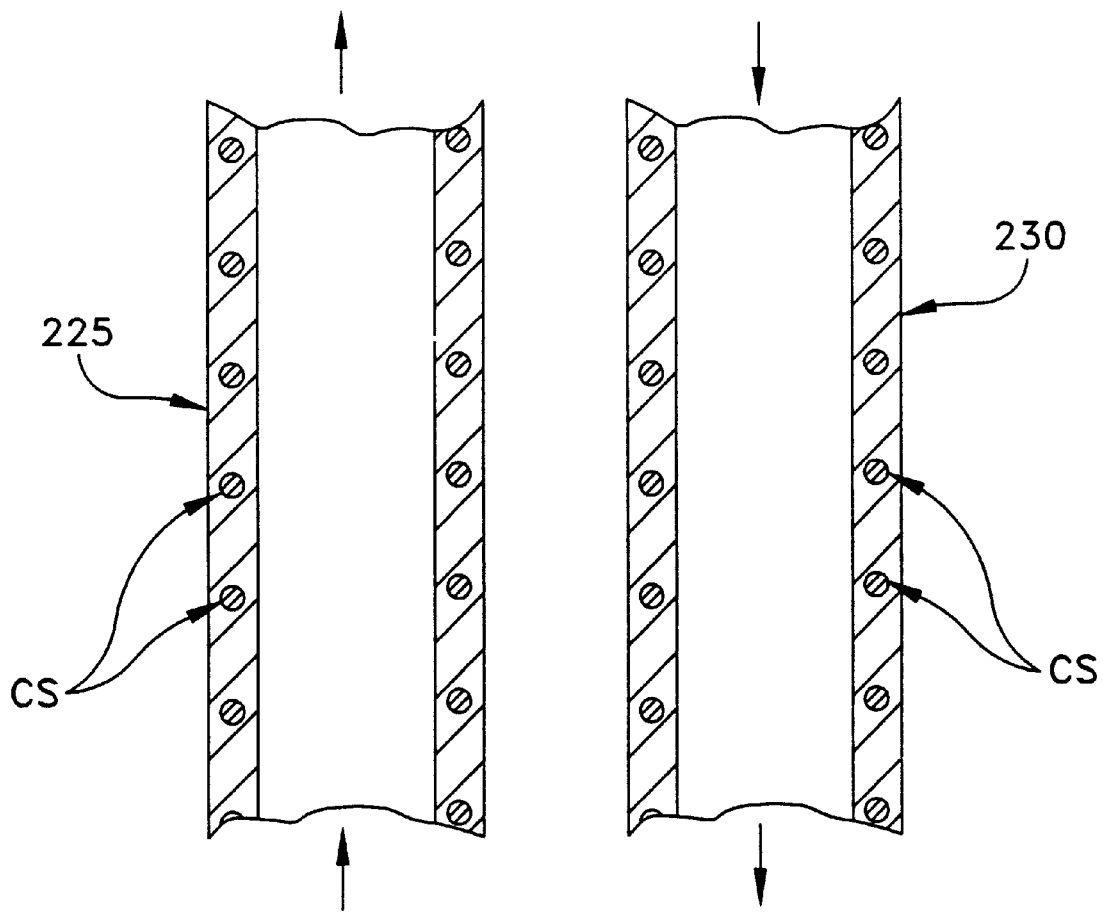
FIG. 32 is a partial sectional view showing yet another novel form of subcutaneous port and catheter assembly.

Look next at FIG. 32, there is shown an embodiment of the present invention which is intended to remedy this problem. More particularly, coiled springs CS may be encapsulated in the side walls of suction line 225 and/or return line 230 so as to provide stiffening to the lines, whereby kinking can be avoided.

It will, of course, be appreciated that various modifications may be made to the preferred embodiments disclosed above without departing from the spirit and scope of the present invention. Accordingly, it is intended that this invention be limited only by the claims ultimately issued from this patent application and/or any patent application(s) claiming priority therefrom.

Advantages of the Invention

Numerous advantages are achieved through the provision and use of the present invention.

For one thing, the present invention provides improved apparatus for use in the dialysis of blood.

And the present invention provides improved apparatus for use in the dialysis of blood, wherein use of the improved apparatus will yield increased operating time between clotting episodes, thereby leading to lower overall medical costs by reducing patient hospitalizations and surgical procedures.

Also, the present invention provides improved apparatus for use in the dialysis of blood, wherein use of the improved apparatus will result in reduced infection problems.

Furthermore, the present invention provides improved apparatus for use in the dialysis of blood, wherein use of the improved apparatus will not tend to increase cardiac output, which in turn tends to place increased stress on the heart of the patient.

And the present invention provides improved apparatus for use in the dialysis of blood, wherein use of the improved apparatus will not require any significant maturation time between the time the apparatus is placed in the body and the time use of the apparatus may commence.

Also, the present invention provides improved apparatus for use in the dialysis of blood, wherein the improved apparatus will be better accepted by the patient.

Furthermore, the present invention provides improved apparatus for use in the dialysis of blood, wherein use of the improved apparatus will not result in post-dialysis bleeding and/or intra-dialysis bleeding.

And the present invention provides improved apparatus for use in the dialysis of blood, wherein use of the improved apparatus will result in less flow obstruction problems.

Also, the present invention provides improved apparatus for use in the dialysis of blood, wherein use of the improved apparatus will result in less air embolism problems.

Furthermore, the present invention provides improved apparatus for use in the dialysis of blood, wherein the improved apparatus will be less likely to be damaged by undesired contact during the periods between dialysis sessions.

And the present invention provides improved apparatus for use in the dialysis of blood, wherein the improved apparatus permits dialysis to be conducted with higher blood flow rates.

And the present invention provides an improved method for the dialysis of blood.

What is claimed is:

1. A subcutaneous port and catheter assembly for use in the dialysis of the blood of a patient, said assembly comprising a connector portion and a catheter portion;

said connector portion comprising a subcutaneous port element adapted for implantation within the body of the patient, said subcutaneous port element comprising an inlet adapted for communication with a percutaneous needle connected to the output port of a dialysis machine, and an outlet adapted for communication with a percutaneous needle connected to the inlet port of a dialysis machine; and said catheter portion comprising a catheter element comprising:

a suction line having a proximal end and a distal end, said proximal end of said suction line being connected to said subcutaneous port element and in communication with said outlet, and said distal end of said suction line terminating in a suction line mouth; and a return line having a proximal end and a distal end, said proximal end of said return line being connected to said subcutaneous port element and in communication with said inlet, and said distal end of said return line terminating in a return line mouth;

said suction line and said return line being adapted for disposition within the body of the patient so that said suction line mouth and said return line mouth are both disposed in the vascular system of the patient, said suction line mouth and said return line mouth being disposed different distances from said connector portion.

2. A subcutaneous port and catheter assembly according to claim 1 wherein said catheter element is constructed so that said return line mouth is spaced from said suction line mouth such that said return line mouth is farther from said subcutaneous port element that said suction line mouth.

3. A subcutaneous port and catheter assembly according to claim 1 wherein said catheter element is constructed so that said suction line mouth is spaced from said return line mouth such that said suction line mouth is farther from said subcutaneous port element that said return line mouth.

4. A subcutaneous port and catheter assembly according to claim 3 wherein:

said suction line has a length facilitating the disposition of said suction line mouth in a first portion of the vascular system of the patient, the first portion being selected from a group of portions consisting of (1) a right atrium portion, and (2) an inferior vena cava portion; and said return line has a length facilitating the disposition of said return line mouth in a second portion of the vascular system of the patient, the second portion being selected from a group of portions consisting of (1) an internal jugular vein portion, and (2) a superior vena cava portion.

5. A subcutaneous port and catheter assembly according to claim 4 wherein said suction line and said return line enter the vascular system of the patient through different openings.

6. A subcutaneous port and catheter assembly according to claim 4 wherein said return line mouth is disposed adjacent to an inside wall of the vascular system of the patient.

7. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal, end of said return line being connected to said connector portion and in communication with said inlet, and said distal end of said return line terminating in a return line mouth;

said suction line and said return line being adapted for disposition within the body of the patient so that said suction line mouth and said return line mouth are both disposed in the vascular system of the patient;

said suction line having a length facilitating the disposition of said suction line mouth in a first portion of the vascular system of the patient, the first portion being selected from a group of portions consisting of (1) a right atrium portion, and (2) an inferior vena cava portion; and said return line having a length facilitating the disposition of said return line mouth in a second portion of the vascular system of the patient, the second portion being selected from a group of portions consisting of (1) an internal jugular vein portion, and (2) a superior vena cava portion.

8. Apparatus according to claim 7 wherein said connector portion comprises a subcutaneous port element adapted for implantation within the body of the patient.

9. Apparatus according to claim 7 wherein said connector portion comprises an extracorporeal connector element adapted for attachment against an outside surface of the body of the patient.

10. Apparatus according to claim 7 wherein said suction line and said return line enter the vascular system of the patient through different openings.

11. Apparatus according to claim 7 wherein said return line mouth is disposed adjacent to an inside wall of the vascular system of the patient.

12. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition within the body of the patient so that said suction line mouth and said return line mouth are both disposed in the vascular system of the patient;

said suction line having a length facilitating the disposition of said suction line mouth in a first portion of the vascular system of the patient, the first portion being selected from a group of portions consisting of (1) a right atrium portion, (2) an inferior vena cava portion, and (3) a superior vena cava portion; and said return line having a length facilitating the disposition of said return line mouth in the right ventricle of the heart.

13. Apparatus according to claim 12 wherein said connector portion comprise a subcutaneous port element adapted for implantation within the body of the patient.

14. Apparatus according to claim 12 wherein said connector portion comprises an extracorporeal connector element adapted for attachment against an outside surface of the body of the patient.

15. Apparatus according to claim 12 wherein said suction line and said return line enter the vascular system of the patient through different openings.

16. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said return line comprises a flange adjacent said return line mouth, and said apparatus further comprises a locking collar for capturing a wall of the vascular system of the patient between said flange and said locking collar.

17. Apparatus according to claim 16 wherein said connector portion comprises a subcutaneous port element adapted for implantation within the body of the patient.

18. Apparatus according to claim 16 wherein said connector portion comprises an extracorporeal connector element adapted for attachment against an outside surface of the body of the patient.

19. Apparatus according to claim 17 wherein said suction line in disposed within said return line.

20. Apparatus according to claim 18 wherein said suction line in disposed within said return line.

21. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:
  a suction line having a proximal end and a distal end, said proximal end of said suction line being connected to said connector portion and in communication with said outlet, and said distal end of said suction line terminating in a suction line mouth; and
  a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said apparatus further comprises a support member interconnecting the distal end of said suction line and an inside wall of the vascular system of the patient so as to position said suction line mouth substantially centrally of the inside wall of the vascular system of the patient.

22. Apparatus according to claim 21 wherein said connector portion comprises a subcutaneous port element adapted for implantation within the body of the patient.

23. Apparatus according to claim 21 wherein said connector portion comprises an extracorporeal connector element adapted for attachment against an outside surface of the body of the patient.

24. Apparatus according to claim 21 wherein said apparatus further comprises a support member interconnecting the distal end of said return line and an inside wall of the vascular system of the patient so as to position said return line mouth substantially centrally of the inside wall of the vascular system of the patient.

25. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:
  a suction line having a proximal end and a distal end, said proximal end of said suction line being connected to said connector portion and in communication with said outlet, and said distal end of said suction line terminating in a suction line mouth; and
  a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of said distal end of said suction line and said distal end of said return line includes a relatively stiff portion to help maintain that line in a selected position within the vascular system of the patient.

26. Apparatus according to claim 25 wherein said connector portion comprises a subcutaneous port element adapted for implantation within the body of the patient.

27. Apparatus according to claim 25 wherein said connector portion comprises an extracorporeal connector element adapted for attachment against an outside surface of the body of the patient.

28. Apparatus according to claim 25 wherein a relatively soft portion is disposed distal to said relatively stiff portion.

29. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:
  a suction line having a proximal end and a distal end, said proximal end of said suction line being connected to said connector portion and in communication with said outlet, and said distal end of said suction line terminating in a suction line mouth; and
  a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of said distal end of said suction line and said distal end of said return line includes projections extending radially therefrom so as to keep that line's mouth spaced some distance away from an inside wall of the vascular system of the patient.

30. Apparatus according to claim 29 wherein said connector portion comprises a subcutaneous port element adapted for implantation within the body of the patient.

31. Apparatus according to claim 29 wherein said connector portion comprises an extracorporeal connector element adapted for attachment against an outside surface of the body of the patient.

32. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of the central lumen of said suction line and the central lumen of said return line is gradually diametrically increased in a flared manner, with that central lumen having a maximum diameter at that line's distal mouth.

33. Apparatus according to claim 32 wherein said connector portion comprises a subcutaneous port element adapted for implantation within the body of the patient.

34. Apparatus according to claim 32 wherein said connector portion comprises an extracorporeal connector element adapted for attachment against an outside surface of the body of the patient.

35. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of said distal end of said suction line and said distal end of said return line includes at least one side opening adjacent that line's mouth whereby fluid may enter that line even if that line's mouth should be occluded.

36. Apparatus according to claim 35 wherein said connector portion comprises a subcutaneous port element adapted for implantation within the body of the patient.

37. Apparatus according to claim 35 wherein said connector portion comprises an extracorporeal connector element adapted for attachment against an outside surface of the body of the patient.

38. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said catheter element is constructed so that said suction line mouth is spaced from said return line mouth such that said suction line mouth is further from said connector portion than said return line mouth; and a sleeve having a first portion disposed around an intermediate portion of said suction line and said distal end of said return line, and a second portion disposed around said suction line distally of said return line, said sleeve second portion being integral with and an extension of said sleeve first portion, said sleeve being made of elastic material such that when said apparatus is not in operation, said sleeve second portion contracts around said suction line and blocks off said return line mouth, and when said apparatus is in operation, said sleeve second portion is opened by outflow from said return line mouth.

39. Apparatus according to claim 38 wherein said connector portion comprises a subcutaneous port element adapted for implantation within the body of the patient.

40. Apparatus according to claim 38 wherein said connector portion comprises an extracorporeal connector element adapted for attachment against an outside surface of the body of the patient.

41. A subcutaneous port and catheter assembly for use in the dialysis of the blood of a patient, said assembly comprising a connector portion and a catheter portion;

said connector portion comprising a subcutaneous port element adapted for implantation within the body of the patient, said subcutaneous port element comprising an inlet adapted for communication with a percutaneous needle connected to the output port of a dialysis machine, and an outlet adapted for communication with a percutaneous needle connected to the input port of a dialysis machine; and said catheter portion comprising a catheter element comprising:
a suction line having a proximal end and a distal end, said proximal end of said suction line being connected to said subcutaneous port element and in communication with said outlet, and said distal end of said suction line terminating in a suction line mouth; and
a return line having a proximal end and a distal end, said proximal end of said return line being connected to said subcutaneous port element and in communication with said inlet, and said distal end of said return line terminating in a return line mouth;
said suction line and said return line being adapted for disposition within the body of the patient so that said suction line mouth and said return line mouth are both disposed in the vascular system of the patient;
said return line being formed out of an elastomeric material such that said return line will collapse down when said apparatus is not in use and expand outward when said apparatus is in use.

42. Apparatus according to claim 41 wherein said suction line and said return line are formed integral with one another.

43. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:
a suction line having a proximal end and a distal end, said proximal end of said suction line being connected to said connector portion and in communication with said outlet, and said distal end of said suction line terminating in a suction line mouth; and
a return line having a proximal end and a distal end, said proximal end of said return line being connected to said connector portion and in communication with said inlet, and said distal end of said return line terminating in a return line mouth;
said suction line and said return line being adapted for disposition relative to the body of the patient so that said suction line mouth and said return line mouth are both disposed in the vascular system of the patient;
and further wherein at least one of the central lumen said suction line and the central lumen of said return line is tapered along its length, with the inner diameter of that line being larger at the proximal end of that line than at the distal end of that line.

44. Apparatus according to claim 43 wherein said connector portion comprises a subcutaneous port element adapted for implantation within the body of the patient.

45. Apparatus according to claim 43 wherein said connector portion comprises an extracorporeal connector element adapted for attachment against an outside surface of the body of the patient.

46. Apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:
a suction line having a proximal end and a distal end, said proximal end of said suction line being connected to said connector portion and in communication with said outlet, and said distal end of said suction line terminating in a suction line mouth; and
a return line having a proximal end and a distal end, said proximal end of said return line being connected to said connector portion and in communication with said inlet, and said distal end of said return line terminating in a return line mouth;
said suction line and said return line being adapted for disposition relative to the body of the patient so that said suction line mouth and said return line mouth are both disposed in the vascular system of the patient;
and further wherein said catheter element comprises a proximal section and a distal section, said proximal section and said distal section being connected together by a coupling element adapted to be positioned at the point where the catheter element enters the vascular system of the patient.

47. Apparatus according to claim 46 wherein said connector portion comprises a subcutaneous port element adapted for implantation within the body of the patient.

48. Apparatus according to claim 46 wherein said connector portion comprises an extracorporeal connector element adapted for attachment against an outside surface of the body of the patient.

49. Apparatus according to claim 47 wherein said coupling element comprises a relatively rigid curved member.

50. Apparatus according to claim 48 wherein said coupling element comprises a relatively rigid curved member.

51. A subcutaneous port and catheter assembly for use in the dialysis of the blood of a patient, said assembly comprising a connector portion and a catheter portion;

said connector portion comprising a subcutaneous port element adapted for implantation within the body of the patient, said subcutaneous port element comprising an inlet adapted for communication with a percutaneous needle connected to the output port of a dialysis machine, and an outlet adapted for communication with a percutaneous needle connected to the input port of a dialysis machine; and said catheter portion comprising a catheter element comprising:
a suction line having a proximal end and a distal end, said proximal end of said suction line being connected to said subcutaneous port element and in communication with said outlet, and said distal end of said suction line terminating in a suction line mouth; and a return line having a proximal end and a distal end, said proximal end of said return line being connected to said subcutaneous port element and in communication with said inlet, and said distal end of said return line terminating in a return line mouth;

said suction line and said return line being adapted for disposition within the body of the patient so that said suction line mouth and said return line mouth are both disposed in the vascular system of the patient;

at least one of the suction line and the return line incorporating a coiled spring therein such that the line will not kink when the line is subjected to significant bending.

52. A method for effecting the dialysis of blood, the method comprising the steps of:

(1) providing a subcutaneous port and catheter assembly for use in the dialysis of the blood of a patient, said assembly comprising a connector portion and a catheter portion;

said connector portion comprising a subcutaneous port element adapted for implantation within the body of the patient, said subcutaneous port element comprising an inlet adapted for communication with a percutaneous needle connected to the output port of a dialysis machine, and an outlet adapted for communication with a percutaneous needle connected to the input port of a dialysis machine; and said catheter portion comprising a catheter element comprising:

a suction line having a proximal end and a distal end, said proximal end of said suction line being connected to said subcutaneous port element and in communication with said outlet, and said distal end of said suction line terminating in a suction line mouth; and a return line having a proximal end and a distal end, said proximal end of said return line being connected to said subcutaneous port element and in communication with said inlet, and said distal end of said return line terminating in a return line mouth;

said suction line and said return line being adapted for disposition within the body of the patient so that said suction line mouth and said return line mouth are both disposed in the vascular system of the patient, said suction line mouth and said return line mouth being disposed different distances from said connector portion;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

53. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition within the body of the patient so that said suction line mouth and said return line mouth are both disposed in the vascular system of the patient;

said suction line having a length facilitating the disposition of said suction line mouth in a first portion of the vascular system of the patient, the first portion being selected from a group of portions consisting of (1) a right atrium portion, and (2) an inferior vena cava portion; and said return line having a length facilitating the disposition of said return line mouth in a second portion of the vascular system of the patient, the second portion being selected from a group of portions consisting of (1) an internal jugular vein portion, and (2) a superior vena cava portion;

(2) placing said suction line mouth and said return line mouth in the vascular system of the patient so that said suction line mouth is disposed in a first portion of the vascular system of the patient, the first portion being selected from a group of portions consisting of (1) a right atrium portion, and (2) an inferior vena cava portion; and so that said return line is disposed in a second portion of the vascular system of the patient, the second portion being selected from a group of portions consisting of (1) an internal jugular vein portion, and (2) a superior vena cava portion;

(3) connecting said outlet to the input port of a dialysis machine, and connecting said inlet to the output port of a dialysis machine; and (4) operating the dialysis machine.

54. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition within the body of the patient so that said suction line mouth and said return line mouth are both disposed in the vascular system of the patient;

said suction line having a length facilitating the disposition of said suction line mouth in a first portion of the vascular system of the patient, the first portion being selected from a group of portions consisting of (1) a right atrium portion, (2) an inferior vena cava portion, and (3) a superior vena cava portion; and said return line having a length facilitating the disposition of said return line mouth in the right ventricle of the heart;

(2) placing said suction line mouth and said return line mouth in the vascular system of the patient so that said suction line mouth is disposed in a first portion of the vascular system of the patient, the first portion being selected from a group of portions consisting of (1) a right atrium portion, (2) an inferior vena cava portion, and (3) a superior vena cava portion; and so that said return line is disposed in the right ventricle of the heart;

(3) connecting said outlet to the input port of a dialysis machine, and connecting said inlet to the output port of a dialysis machine; and (4) operating the dialysis machine.

55. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said return line comprises a flange adjacent said return line mouth, and said apparatus further comprises a locking collar for capturing a wall of the vascular system of the patient between said flange and said locking collar;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

56. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said apparatus further comprises a support member interconnecting the distal end of said suction line and an inside wall of the vascular system of the patient so as to position said suction line mouth substantially centrally of the inside wall of the vascular system of the patient;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

57. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of said distal end of said suction line and said distal end of said return line includes a relatively stiff portion to help maintain that line in a selected position within the vascular system of the patient;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

58. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of said distal end of said suction line and said distal end of said return line includes projections extending radially therefrom so as to keep that line's mouth spaced some distance away from an inside wall of the vascular system of the patient;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

59. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of the central lumen of said suction line and the central lumen of said return line is gradually diametrically increased in a flared manner, with that central lumen having a maximum diameter at that line's distal mouth;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

60. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of said distal end of said suction line and said distal end of said return line includes at least one side opening adjacent that line's mouth whereby fluid may enter that line even if that line's mouth should be occluded;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

61. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said catheter element is constructed so that said suction line mouth is spaced from said return line mouth such that said suction line mouth is further from said connector portion than said return line mouth; and a sleeve having a first portion disposed around an intermediate portion of said suction line and said distal end of said return line, and a second portion disposed around said suction line distally of said return line, said sleeve second portion being integral with and an extension of said sleeve first portion, said sleeve being made of elastic material such that when said apparatus is not in operation, said sleeve second portion contracts around said suction line and blocks off said return line mouth, and when said apparatus is in operation, said sleeve second portion is opened by outflow from said return line mouth;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

62. A method for effecting the dialysis of blood, the method comprising the steps of:

(1) providing a subcutaneous port and catheter assembly for use in the dialysis of the blood of a patient, said assembly comprising a connector portion and a catheter portion;

said connector portion comprising a subcutaneous port element adapted for implantation within the body of the patient, said subcutaneous port element comprising an inlet adapted for communication with a percutaneous needle connected to the output port of a dialysis machine, and an outlet adapted for communication with a percutaneous needle connected to the input port of a dialysis machine; and said catheter portion comprising a catheter element comprising:

a suction line having a proximal end and a distal end, said proximal end of said suction line being connected to said subcutaneous port element and in communication with said outlet, and said distal end of said suction line terminating in a suction line mouth; and a return line having a proximal end and a distal end, said proximal end of said return line being connected to said subcutaneous port element and in communication with said inlet, and said distal end of said return line terminating in a return line mouth;

said suction line and said return line being adapted for disposition within the body of the patient so that said suction line mouth and said return line mouth are both disposed in the vascular system of the patient;

said return line being formed out of an elastomeric material, such that said return line will collapse down when said apparatus is not in use and expand outward when said apparatus is in use;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

63. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of an dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein at least one of the central lumen of said suction line and the central lumen of said return line is tapered along its length, with the inner diameter of that line being larger at the proximal end of that line than at the distal end of that line;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

64. A method for effecting the dialysis of blood, the method comprising the steps of:

(1) providing apparatus for use in the dialysis of the blood of a patient, said apparatus comprising a connector portion and a catheter portion;

said connector portion comprising an inlet adapted for communication with a line connected to the output port of a dialysis machine, and an outlet adapted for communication with a line connected to the input port of a dialysis machine; and said catheter portion comprising a catheter element comprising:

a suction line having a proximal end and a distal end, said proximal end of said suction line being connected to said connector portion and in communication with said outlet, and said distal end of said suction line terminating in a suction line mouth; and a return line having a proximal end and a distal end, said proximal end of said return line being connected to said connector portion and in communication with said inlet, and said distal end of said return line terminating in a return line mouth;

said suction line and said return line being adapted for disposition relative to the body of the patient so that said suction line mouth and said return line mouth are both disposed in the vascular system of the patient;

and further wherein said catheter element comprises a proximal section and a distal section, said proximal section and said distal section being connected together by a coupling element adapted to be positioned at the point where the catheter element enters the vascular system of the patient;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

65. A method according to claim 64 wherein said distal section of said catheter element is connected to said coupling element before said proximal section of said catheter element is connected to said coupling element.

66. A method for effecting the dialysis of blood, the method comprising the steps of:

(1) providing a subcutaneous port and catheter assembly for use in the dialysis of the blood of a patient, said assembly comprising a connector portion and a catheter portion;

said connector portion comprising a subcutaneous port element adapted for implantation within the body of the patient, said subcutaneous port element comprising an inlet adapted for communication with a percutaneous needle connected to the output port of a dialysis machine, and an outlet adapted for communication with a percutaneous needle connected to the input port of a dialysis machine; and said catheter portion comprising a catheter element comprising:

a suction line having a proximal end and a distal end, said proximal end of said suction line being connected to said subcutaneous port element and in communication with said outlet, and said distal end of said suction line terminating in a suction line mouth; and a return line having a proximal end and a distal end, said proximal end of said return line being connected to said subcutaneous port element and in communication with said inlet, and said distal end of said return line terminating in a return line mouth;

said suction line and said return line being adapted for disposition within the body of the patient so that said suction line mouth and said return line mouth are both disposed in the vascular system of the patient;

at least one of the suction line and the return line incorporating a coiled spring therein such that the line will not kink when the line is subjected to significant bending;

(2) placing said suction line mouth and said return line mouth in the vascular system of the patient;

(3) connecting said outlet to the input port of a dialysis machine, and connecting said inlet to the output port of a dialysis machine; and (4) operating the dialysis machine.

* * * * *